United States Patent
Rothberg et al.

(10) Patent No.: US 9,062,304 B2
(45) Date of Patent: Jun. 23, 2015

(54) SPATIALLY INHOMOGENOUSLY FUNCTIONALIZED POROUS MEDIA AND METHOD FOR USE IN SELECTIVE REMOVAL OF CONTAMINANTS

(75) Inventors: Lewis Rothberg, Pittsford, NY (US); Barbara Stwertka, Rochester, NY (US)

(73) Assignee: The University of Rochester, Rochester, NY (US)

( * ) Notice: Subject to any disclaimer, the term of this patent is extended or adjusted under 35 U.S.C. 154(b) by 96 days.

(21) Appl. No.: 12/704,277

(22) Filed: Feb. 11, 2010

(65) Prior Publication Data

US 2010/0267109 A1  Oct. 21, 2010

Related U.S. Application Data

(60) Provisional application No. 61/151,551, filed on Feb. 11, 2009.

(51) Int. Cl.
*C12Q 1/68* (2006.01)
*C12M 1/34* (2006.01)
*B01L 3/00* (2006.01)
*G01N 31/22* (2006.01)
*C07H 21/02* (2006.01)
*B32B 3/26* (2006.01)
*C12N 15/10* (2006.01)

(52) U.S. Cl.
CPC .................................. *C12N 15/1006* (2013.01)

(58) Field of Classification Search
CPC .......... C12Q 1/68; C12Q 1/6806; B32B 3/26; B01J 2219/00722

USPC ............... 435/6.1, 287.2; 422/430; 536/23.1; 428/315.5

See application file for complete search history.

(56) References Cited

U.S. PATENT DOCUMENTS

| | | | |
|---|---|---|---|
| 6,582,942 B1 | 6/2003 | Christensen et al. | |
| 2002/0160139 A1* | 10/2002 | Huang et al. | 428/36.9 |
| 2004/0016702 A1* | 1/2004 | Hennessy et al. | 210/660 |
| 2004/0018559 A1* | 1/2004 | Lau et al. | 435/7.1 |
| 2006/0160122 A1* | 7/2006 | Harrold et al. | 435/6 |
| 2007/0155021 A1 | 7/2007 | Zhang et al. | |
| 2008/0026451 A1 | 1/2008 | Braman et al. | |

FOREIGN PATENT DOCUMENTS

| | | |
|---|---|---|
| EP | 0691148 A2 | 1/1996 |
| WO | 2009155128 A1 | 12/2009 |

OTHER PUBLICATIONS

AmpliTaq PCR master mix data sheets [Downloaded from the internet, www.appliedbiosystems.com], pp. 1-30, printed on Sep. 23, 2013.*

* cited by examiner

*Primary Examiner* — Narayan Bhat
(74) *Attorney, Agent, or Firm* — Hodgson Russ LLP

(57) ABSTRACT

Compositions and methods for separating double-stranded nucleic acids out of a mixture comprising single-stranded nucleic acids and/or dNTPs and/or enzymes. The method uses spatially inhomogenously functionalized nanoporous materials. For example, the compositions and methods of the present invention can be used to purify DNA amplification reaction products.

12 Claims, 7 Drawing Sheets

INNER (PORE) SURFACE

| | Hydrophobic (H) | Charged (C) | Specific binding (S) | Resistant (R) | |
|---|---|---|---|---|---|
| OUTER SURFACE | Inner more/outer less: | • Hybridization assay (remove unbound short ss probe oligo, retain ss hybridized to large target such as PCR) | | | H |
| | • Hybridization assay (H interior and – exterior) | • Hybridization assay (+ interior and – exterior)<br>• PCR cleanup | | | C |
| | • Hybridization assay (remove unbound ss, retain hybridized ss even with small target)<br>• Enzymatic rxn cleanup | • Nucleotide Removal or big dye sequencing rxn cleanup (Remove dNTP while retaining ss-fragments)<br>• Hybridization assay<br>• Enzymatic rxn or PCR cleanup<br>• Remove unattached dye in tagging reactions while keeping tagged biomolecules | • Remove small m-RNA from total RNA<br>• Increase specificity of mi-RNA detection | • Concentration of large molecules via water retention in pores | R |

Figure 10

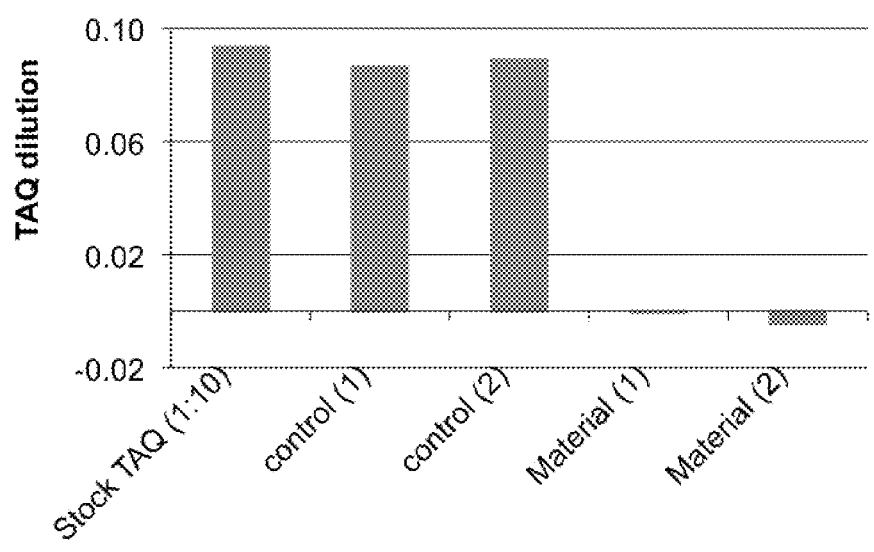

Figure 11

```
                       SEQUENCE LISTING

<160> NUMBER OF SEQ ID NOS: 6

<210> SEQ ID NO 1
<211> LENGTH: 20
<212> TYPE: DNA
<213> ORGANISM: artificial sequence
<220> FEATURE:
<223> OTHER INFORMATION: strand of annealed self-complementary ss-DNA

<400> SEQUENCE: 1
taatacgact cactataggg                                                20

<210> SEQ ID NO 2
<211> LENGTH: 18
<212> TYPE: DNA
<213> ORGANISM: artificial sequence
<220> FEATURE:
<223> OTHER INFORMATION: single strand of annealed self-complementary
      ss-DNA

<400> SEQUENCE: 2
atcgtcctgc aggacgat                                                  18

<210> SEQ ID NO 3
<211> LENGTH: 24
<212> TYPE: DNA
<213> ORGANISM: artificial sequence
<220> FEATURE:
<223> OTHER INFORMATION: forward PCR primer for amplification of Lambda
      DNA template

<400> SEQUENCE: 3
tgaaacgctt gctgcaacgc caaa                                           24

<210> SEQ ID NO 4
<211> LENGTH: 30
<212> TYPE: DNA
<213> ORGANISM: artificial sequence
<220> FEATURE:
<223> OTHER INFORMATION: reverse primer for PCR amplification of Lambda
      DNA template

<400> SEQUENCE: 4
aaagcaattg gcggtgatgt aaacactatg                                     30

<210> SEQ ID NO 5
<211> LENGTH: 24
<212> TYPE: DNA
<213> ORGANISM: Lambda phage
```

```
<400> SEQUENCE: 5
gccaaaggcg gttaaggtgg taat                                    24

<210> SEQ ID NO 6
<211> LENGTH: 20
<212> TYPE: DNA
<213> ORGANISM: artificial sequence
<220> FEATURE:
<223> OTHER INFORMATION: T7 sequence primer

<400> SEQUENCE: 6
taatacgact cactataggg                                         20
```

SPATIALLY INHOMOGENOUSLY FUNCTIONALIZED POROUS MEDIA AND METHOD FOR USE IN SELECTIVE REMOVAL OF CONTAMINANTS

CROSS-REFERENCE TO RELATED APPLICATIONS

This application claims priority to U.S. provisional patent application no. 61/151,551, filed Feb. 11, 2009, the disclosure of which is incorporated herein by reference.

STATEMENT REGARDING FEDERALLY SPONSORED RESEARCH

This invention was made with government support under contract no. RR024968 awarded by the National Institutes of Health. The government has certain rights in the invention.

FIELD OF THE INVENTION

The present invention relates to compositions and methods for isolating desired biomolecules from a mixture of biomolecules. In one embodiment, the present invention relates to compositions and methods for isolating double-stranded nucleic acids from mixtures comprising double-stranded nucleic acids, single-stranded nucleic acids and free nucleotides.

BACKGROUND OF THE INVENTION

In the analysis of biological materials, it is often necessary to first isolate or purify molecules of interest from a mixture of molecules such as found in a biological sample. While different molecules can be separated based on their chemical properties, such separation methods can be tedious and time consuming. In the analysis of nucleic acid molecules, if the desired molecules are not sufficient to be detected easily, techniques can be used to increase their copy numbers for easy detection.

For example, DNA analysis and sequencing typically involves increasing the copy number of a targeted portion of the genome by PCR amplification. Cleanup of PCR products to remove primers and dNTP is necessary prior to sequencing because residual primers can act as extension primers during sequencing and produce dye-labeled sequence fragments that can complicate data interpretation or, worse, lead to false conclusions. Further, failure to remove dNTP can result in suboptimal ratios of dNTP to labeled ddNTP (di-deoxynucleotides) used to regulate read lengths in sequencing reactions. Similar considerations apply to removal of unextended primers from samples prior to MALDI-TOF analysis.

Conventional approaches to PCR cleanup generally rely on immobilization of DNA amplicons, primers and dNTP on solid supports (e.g., membranes or magnetic particles), typically using chaotropic salts, and then selectively eluting undesired components off these surfaces in various solvents until the desired component is eluted. These multiple step processes are time-consuming, labor intensive and introduce undesirable components such as organic solvents and chaotropic salts that interfere with subsequent reactions and therefore require further cleanup.

In order to improve usability of polymerase chain reaction (PCR) amplicons for downstream applications, it is desirable to remove excess primers and unincorporated deoxynucleotide triphosphates (dNTPs) in a more efficient manner while retaining the amplified double-stranded (ds) DNA (nucleic acids).

BRIEF SUMMARY OF THE INVENTION

In one aspect, the present invention provides compositions and methods separating biomolecules from a mixture of biomolecules. In one embodiment, the present invention provides compositions and methods for separating double-stranded nucleic acids out of a mixture comprising single-stranded and/or free (individual) nucleic acids. As an example, this method can be used to separate double-stranded DNA from mixtures obtained in DNA amplification reactions.

In one embodiment, the present invention provides a method for separating double-stranded nucleic acids from a mixture comprising double stranded nucleic acids (e.g., DNA), single-stranded nucleic acids and/or free nucleotides in an aqueous solution. The mixture can also comprise enzymes. The mixture is contacted with a spatially inhomogenously functionalized nanoporous material, where the surface of the spatially inhomogenously functionalized nanoporous material comprises pore surface and non-pore surface and where the pore surface has surface groups of one functionality and the non-pore surface has surface groups of a different functionality. The aqueous solution and nanoporous material are incubated under conditions such that the single-stranded nucleic acids and/or free nucleotides are selectively adsorbed to the pore surface. The nanoporous material is isolated from the aqueous solution, thus separating the double stranded nucleic acids from the single-stranded nucleic acids and/or free nucleotides.

For example, the double-stranded nucleic acids are separated such that the aqueous solution comprises less than 10%, 5%, 2%, or 1% single-stranded nucleic acids and/or free nucleotides, and if enzymes are present in the mixture, and/or enzymes.

The pore surface can be functionalized with positively-charged compounds selected from the group consisting of amines, imines, metal-ion containing compounds and combinations thereof and/or hydrophobic compounds to provide surface groups of one functionality, and the non-pore surface can be functionalized with negatively-charged compounds selected from the group consisting of anionic compounds, polyanionic compounds, polyelectrolytes, and combinations thereof and/or hydrophobic and/or adsorption resistant compounds to provide surface groups of a different functionality.

The spatially inhomogenously functionalized nanoporous material be comprised of at least two independent spatially inhomogenously functionalized nanoporous materials, and the independent spatially inhomogenously functionalized nanoporous materials exhibit different pore surface functionality and/or different non-pore functionality.

In another aspect, the present invention provides a composition comprising an inhomogenously functionalized nanoporous material, wherein the surface of the inhomogenously functionalized nanoporous material comprises pore surface and non-pore surface, wherein the pore surface has surface groups of one functionality and the non-pore surface has surface groups of a different functionality, wherein the nanoporous material has pores of 2 to 300 nm in diameter. The nanoporous material can be, for example, porous silica, porous alumina, or zeolite.

In one embodiment, the pore surface of the inhomogenously functionalized nanoporous material is functionalized with positively-charged compounds, such as, for example, amines, imines, metal-ion containing compounds, and/or hydrophobic compounds to provide surface groups of one functionality, and the non-pore surface is functionalized with negatively-charged compounds such as, for example, anionic-compounds, polyanionic compounds, polyelectrolytes, and/or hydrophobic compounds and/or adsorption resistant compounds to provide surface groups of a different functionality.

BRIEF DESCRIPTION OF THE FIGURES

FIG. 10. Table summarizing several of the nucleic acid purification and assay applications which can be performed using the materials and protocols described herein.

FIG. 11. Data showing removal of an enzyme (Taq DNA polymerase) from solution.

DETAILED DESCRIPTION OF THE INVENTION

In one aspect, the present invention provides compositions and methods separating biomolecules from a mixture of biomolecules. In one embodiment, the present invention provides compositions and methods for separating double-stranded nucleic acids out of a mixture comprising single-stranded and/or free (individual) nucleic acids. In one embodiment, the present invention provides compositions and methods for purifying double-stranded nucleic acids from other components of typical nucleic acid amplification reactions, such as primers, dNTPs, and/or enzymes (e.g., polymerase) and the like.

Figure 1A:
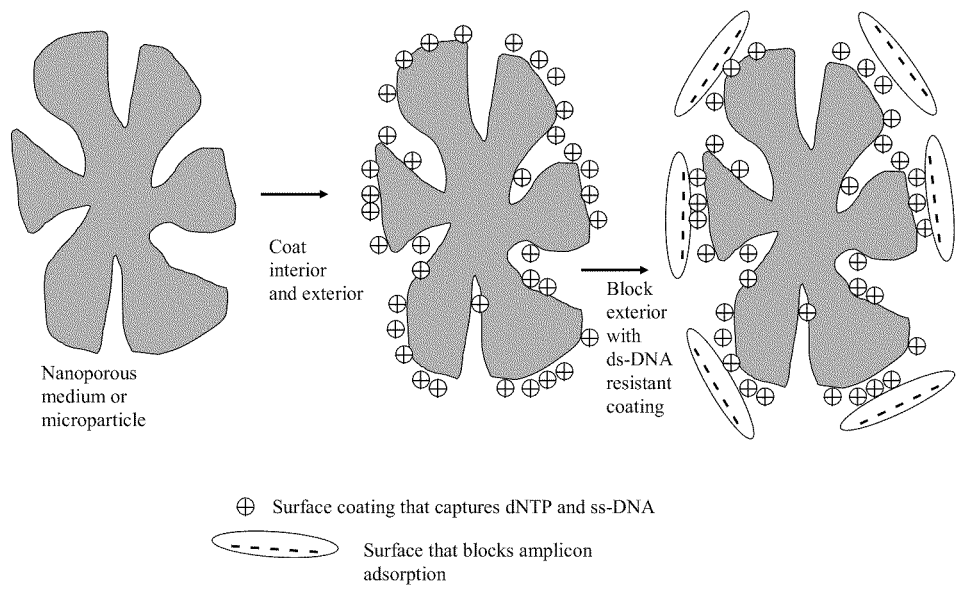
FIG. 1(a). General approach to spatially inhomogeneous coatings

The method of double-stranded nucleic acid separation is based on the use of nanoporous materials in which the internal surfaces (pore surfaces) are functionalized to adsorb small molecules (primers and dNTPs) and the external surfaces (non-pore surfaces) are functionalized to inhibit adsorption of the larger molecules (double-stranded PCR amplicons)—illustrated in FIG. 1(a). Since the larger dsDNA is excluded from the interior of the pores, only the small molecules will be adsorbed to the nanoporous materials and thus, double-stranded DNA can be purified from the mixtures by exploiting differential functionalization of interior and exterior surfaces as illustrated in FIG. 1(a).

In one embodiment, the present invention provides a method for separating double-stranded nucleic acids out of a mixture comprising single-stranded nucleic acids and/or free nucleotides by using spatially inhomogenously functionalized nanoporous material. The surface of the spatially inhomogenously functionalized nanoporous material comprises pore surface and non-pore surface. The pore surface has surface groups of one functionality and the non-pore surface has surface groups of a different functionality. The method comprises the steps of: a) contacting a mixture comprising double stranded nucleic acids, single-stranded nucleic acids and/or free nucleotides in an aqueous solution with the spatially inhomogenously functionalized nanoporous material; b) incubating the aqueous solution and nanoporous material from a) under conditions such that the single-stranded nucleic acids and/or free nucleotides are selectively adsorbed on the pore surface; and c) isolating the nanoporous material from the aqueous solution thereby separating the double stranded nucleic acids (which remain in solution) from the single-stranded nucleic acids and/or free nucleotides.

In identifying suitable nanoporous materials from which spatially inhomogenously functionalized nanoporous materials can be prepared, the size of the small molecules which are desired to be removed (i.e., contaminants such as, for example the primer dimers and dNTPs in a mixture obtained in a PCR reaction) is taken into consideration. The pores comprise an opening in the external surface (i.e., orifice) of the nanoporous material and an inner pore surface. Material (e.g., a solution) can access the pore only via the pore opening.

Suitable pores will also exclude larger molecules such as double-stranded DNA amplicons that can be several tens to hundreds of base pairs in length, and therefore, several tens of nm in spatial extent. It is believed that the longer persistence length of double-stranded DNA (the average distance over which DNA adopts a straight-line trajectory in three-dimensional space) also facilitates the exclusion of such DNA relative to single-stranded DNA which can fold more readily and therefore easily diffuse into nanoporous materials.

Nanoporous material (also referred to herein as beads) useful in the present invention and have surfaces which can be functionalized. Suitable materials have a high surface area. Materials such as gel or foams (such as, for example, sol-gel materials, xerogels and aerogels) can be used. The materials can be particulate (such as, for example, silica gel) or gel or foam layers on a solid substrate (such as, for example, a spherical substrate or planar substrate). Suitable nanoporous particulate materials include porous silica, porous alumina, porous titania and zeolites. Suitable high surface area gels/foams include silica, alumina, titania, hafnia, germania and zeolites. Also, mixed oxides can be used.

In one embodiment, the nanoporous material is porous silica particles. Suitable nanoporous materials are commercially available silica gels. The silica particles are about 10 to 500 microns, including all integers therebetween, in diameter.

In one embodiment, the refractive index of the nanoporous material is selected based on the choice of metal oxide or mixed metal oxide.

The nanoporous materials are comprised of pores. The size of the pore opening as used herein refers to the length of the longest axis of the pore opening. For example, if the pore opening is circular or can be approximated by a circle, the size of the pore opening is the diameter of the circle. Suitable nanoporous materials have pore sizes of approximately 2 nm to 300 nm. For example, pores of this size allow adequate access for the contaminants into the pores. It is not necessary that all the pores in the nanoporous materials be of the same size. In various embodiments, the nanoporous material comprise pores, where the majority of pore diameters, more preferably, 70, 80, 90 or 95% fall within 10% or 5% of the nominal pore size. The nominal pore size can be from 2 to 300 nm, including all integers therebetween.

An example of a suitable nanoporous particulate material is chromatography grade nanoporous silica which can be obtained as a substantially spherical particle with a diameter of 40 to 60 microns, and a pore size of approximately 60 Å. A material with these characteristics is commercially available, such as Merck 9385 silica gel.

Other examples of suitable nanoporous materials include Silica gel Davisil®, Grade 633, pore size 60 Å, 200-425 mesh, Silica gel Davisil®, Grade 634, pore size 60 Å, 100-200 mesh, Silica gel Davisil®, Grade 635, pore size 60 Å, 60-100 mesh, Silica gel Davisil®, Grade 636, pore size 60 Å, 35-60 mesh, Silica gel Davisil®, Grade 643, pore size 150 Å, 200-425 mesh, Silica gel Davisil®, Grade 644, pore size 150 Å, 100-200 mesh, Silica gel Davisil®, Grade 645, pore size 150 Å, 60-100 mesh, Silica gel Davisil®, Grade 646, 35-60 mesh, pore size 150 Å, Silica gel Grade 12, pore size 22 Å, 28-200 mesh, Silica gel Grade 62, pore size 150 Å, 60-200 mesh, Silica gel Grade 62, pore size 150 Å, 60-200 mesh, and Silica gel Grade 923, pore size 30 Å, 100-200 mesh, all of which are commercially available.

FIG. 1(a) provides an illustration of spatially inhomogeneous functionalization of a nanoporous material. "Spatially inhomogenously functionalized" or "spatially inhomogeneous functionalization" is intended to mean that the nanoporous material comprises at least two surfaces with each surface bearing at least one functional group which is distinct from the other surface(s) and hence, the surface(s) have different functionality.

In one embodiment, the nanoporous materials comprises pore surface bearing surface group having functionality (and as a result i.e., character) and non-pore surface bearing surface groups having a different functionality (i.e., character). For example, the functional groups on the surface result in the surface having a positively-charged character, a negatively-charged character, a hydrophilic character, a hydrophobic character, an adsorption resistant character, or any combination of these characters. The pore-surfaces are generally inaccessible to the polymers used to functionalize the non-pore surface.

In one embodiment, to achieve selective removal of contaminants from nucleic acid amplification reactions, the pores of the nanoporous materials are coated (i.e., functionalized such that the functionalized surface has groups of a particular functionality) so as to adsorb dNTP, primers and single strands while the exterior of the nanoporous materials (the non-pore surface) is made resistant to amplicon adsorption. This results in spatially inhomogeneous functionalization of the materials.

In another embodiment, different nanopores are functionalized with different materials providing some functionalized nanopore surface which is effective at removing dNTP and other functionalized surface that is effective at removing ssDNA. In yet another embodiment, two sets of functionalized nanoporous materials can be used—one set being functionalized with one material (such as to remove dNTP and primers) and another set being functionalized with another material (such as to remove ssDNA).

A nanoporous surface, either a pore surface or a non-pore surface, can be functionalized such that it has surface groups that render the surface positively-charged, negatively-charged, hydrophilic, hydrophobic, adsorption resistant. A nanoporous surface can also be functionalized such that it has combination of these characters/moities.

Any compound with a functional group capable of having a positive charged can be used to functionalize a nanoporous materials surface such that the surface is rendered positively charged. For example, compounds with functional groups having an appropriate pKa, and thus, retain protons in solution, can be used functionalize a nanoporous material surface (e.g., a nanoparticle pore surface) with groups having a positive-charge functionality. As another example, to impart a positive charge to the nanoporous material surface (e.g., a nanoparticle pore surface) amine-, imine-, thiol- or metal-ion containing compounds can be used.

Amine-containing compounds include, but are not limited to, any compounds with primary, secondary or tertiary amine groups. For compounds with alkyl substituted amine groups, the alkyl groups can, for example, be branched or linear and have, for example, from 1 to 20 carbons. Examples of amine-containing compounds include, for example, aminosilanes with primary, secondary and tertiary amines. Suitable aminosilanes also include those with multiple amine groups. An example of an aminosilane is aminopropyltrimethoxysilane (APTMS), which is commercially available. Another example of an amine-containing compound is a polymer which has amine groups Imine-containing compounds include, but are not limited to, any compound with an imine-group. An example of an imine-containing compound is polyethyleneimine (PEI), which is commercially available, and dimethoxymethylsilylpropyl modified (polyethyleneimine), which is also commercially available.

A metal-ion containing compound can be any metal-ion containing compound, such as, for example, an organometallic compound (e.g., ferrocene) or coordination compound (e.g., ruthenium tris(bipy) or metal-containing macrocycles).

The nanoporous material can be functionalized such that a surface of the material bears functional groups rendering the surface hydrophobic. Examples of hydrophobic functional groups include, for example, hydrocarbon groups (such as lower alkane groups (e.g., $C_4$ to $C_{40}$) which can be branched or linear, cyclohydrocarbon groups (such as cyclohexyl groups), aromatic groups (such as phenyl and benzyl groups) and the like). These hydrophobic groups can be fluorinated (e.g., polytetrafluoroethylene). For example, a compound with any of these groups can be used to functionalize a nanoporous surface rendering the surface hydrophobic. For example, pore surfaces can be endowed with functionally hydrophobic character from the point of view of adsorbing small hydrophobic species and yet still have a sufficient number of unreacted surface groups (e.g, hydroxyl groups (—OH)) that are hydrophilic so that the particles made in this way can remain water soluble.

In one embodiment, the pore surface is functionalized such that it has hydrophobic character. For example, the pore surface can be functionalized with octadecyltrichlorosilane (OTS) or polytetrafluoroethylene (PTFE) which would result in the pore surface bearing groups rendering the surface hydrophobic. Other examples of compounds that can be used to functionalize a surface providing a hydrophobic surface include, but are not limited to, n-butyltrimethoxysilane (C4 alkane surface groups), cyclooctyltrichlorosilane (cyclooctane surface groups), phenoxypropyltricchlorosilane (phenyl surface groups) and nonafluorohexyltrimethoxysilane (partially fluorinated chains as surface groups). As a specific example, OTS modified porous silica particles where OTS coverages of 30-70% render regions of the surface hydrophobic such that they adsorb hydrophobic materials such as single-stranded DNA and enzymes under a wide range of both salt and pH conditions while the silica particles remain dispersed in an aqueous solution.

In one embodiment, the pore surface can be functionalized with positively-charged and/or hydrophobic compounds. The positively-charged or hydrophobic compounds adsorb contaminates, such as dNTPs, primers, ssDNA, and the like. When these compounds are used to functionalize the pore surface they are referred to as "pore functionalizing materials".

Anion-containing compounds include any negatively-charged compound or compound bearing a negatively-charged group/moiety (e.g., carboxylate group, sulfonate group, phosphate group, hydroxide group and the like). Examples of negatively-charged compounds include, but are not limited to, 3(-cyanobutyl)dimethylchlorosilane and methoxyethoxyundecyltrichlorosilane. Polyanionic compounds include compounds bearing more than one negatively-charged group/moiety (e.g. carboxylate group, sulfonate group, phosphate group, hydroxide group and the like). Anionic polyelectrolytes include polymers (and co-polymers, where the co-polymer may comprise monomers that do not have negatively charged groups (e.g., a PAA-polyethylene copolymer)) comprising monomers with negatively-charged groups. Examples of anionic polyelectrolytes include poly(styrene sulfonic acid), poly(acrylic acid) and the like.

The polyelectrolyte compounds can be modified to include hydrophobic groups prior to or after functionalizing a surface. For example, carboxylate groups of PAA can be reacted to form fluorocarbon groups or other hydrophobic groups prior to functionalizing a surface.

In one embodiment, a high molecular weight poly(acrylic acid sodium salt) (PAA) is used as the polyelectrolyte. In another embodiment, sulfonated polystyrene is used as the polyelectrolyte.

The nanoporous material surface(s) can be functionalized with compounds that resist adsorption of ds nucleic acids, e.g., DNA PCR amplicons, which diffuse poorly into the nanopores. When such compounds are used to functionalize the external or non-pore surface they are referred to as "external or non-pore surface functionalizing materials". Suitable adsorption resistant materials include charged (positive or negative) and/or hydrophilic compounds, or any compound known to be resistant to adsorption of biomolecules (e.g., polyethylene glycol). Examples of such compounds include, for example, polyethylene glycol (PEG), and compounds containing polyethylene glycol (e.g., a PEG functionalized silane), and fluorine-containing compounds. Suitable PEG and PEG-containing compounds have from 1 to 100 ethylene glycol groups. Suitable PEG and PEG-containing compounds for functionalization of the non-pore surface have a molecular weight (or hydrodynamic radii) such that the PEG or PEG-containing compound does not enter the pore.

In one embodiment, the positive and/or negative charge on the pore and/or non-pore surface results from exposure of the surface to an aqueous solution of an appropriate pH such that the compound is protonated (resulting in a positively-charged surface) and/or negative (resulting in a negatively-charged surface). For example, an appropriate pH can be 5 to 10, including all integers and values to 0.1 therebetween.

The non-pore surface can be functionalized regardless of which pore surface property is selected. Assuming the pore surface has a positive character (e.g., the pore surface is functionalized with an amine), the non-pore surface can be modified to have negative, hydrophobic, adsorption resistance or selective recognition character).

The pore surface can be negatively charged and the non-pore surface have a different surface character. For example, in the case of silica, the pore surfaces could be rendered negative by covalent attachment of carboxylated silanes or any of the negatively-charged compounds discussed herein. Subsequent treatment of this silica with high MW PAH or polylysine that cannot penetrate the pores would render the exterior non-pore surfaces positive while reactions with aminated PEG or aminated hydrophobic compounds like octadecyl amine (ODA) could make the exterior surfaces adsorption resistant or hydrophobic respectively.

An example is a case where there are two materials with high MW in an analyte solution, and it is desirable to remove only one analyte and concentrate the other. This can be accomplished by treating the solution with a nano-porous materials functionalized such that it selectively adsorbs the undesired analyte component. As a specific example, hydrophobic proteins can be separated from hydrophilic DNA while concentrating the DNA using nanoporous materials functionalized such that the pore surface is adsorption resistant and the non-pore surface is hydrophobic. The protein may have positively-charged regions that would adsorb on a negatively-charged exterior surface while the DNA would not adsorb.

The non-pore surface can be functionalized with, for example, amine terminated synthetic DNA oligonucleotide can be conjugated to carboxylate groups on the PAA functionalized non-pore surface insuring that DNA oligonucleotide moiety would be present only on the non-pore surface. Conjugation of the DNA oligonucleotide can be performed before or after functionalization of the non-pore surface with PAA.

The pore surface of a nanoporous material can also be functionalized with target nucleic acid sequences, and such a material can, for example, be used to extract a particular component from a mixture of small and large molecules in solution (e.g., removal of a particular sequence of oligonucleotide from a mixture of small oligonucleotides).

As a specific example, it may be desirable to separate a particular mi-RNA from a heterogeneous RNA-containing solution or removal of a particular primer set during nested PCR. The pore surface can be functionalized with the complementary oligonucleotide and the non-pore surface functionalized with a high MW material. To functionalize the pore surface with a complementary oligonucleotide, the pore surface can be functionalized with an amine-modified oligonucleotides which was previously functionalized with an epoxy group using silanization chemistry. The epoxide group can react with the amine group of the amine-modified oligonucleotide resulting in functionalization of the pore surface. The non-pore surface can be functionalized such that it is rendered adsorption resistant by covalent attachment of high MW aminated PEG with unreacted epoxides. Alternatively, the non-pore surface can functionalized with positively-charged groups by electrostatic self-assembly of high MW amine-containing polyelectrolytes (e.g., PAH) or with negatively-charged groups by reaction with PAA followed by reaction with PAH.

Selection of pore size and high MW polymers can be carried out to selectively collect particular small species of interest from a complex analyte. The general protocol can be implemented to retain the collected species or to retain the purified solution that no longer contains the collected species.

In another aspect, the present invention provides a general strategy for differentially functionalizing the pore and non-pore surface of a nanoporous material. In general, the non-pore surface is functionalized by reaction/exposure to large macromolecular (typically high molecular weight polymers) materials that do not readily fit into the pores, and thus, only functionalize the non-pore surface. Functionalization of the non-pore surface can be done either before or after that of the pore surface, and there are advantages to either approach. For example, functionalization of the non-pore surface can be achieved either through covalent attachment such as silanization chemistry on porous oxides or via electrostatic self-assembly as for example adsorption of polyelectrolytes on charged surfaces such as hydroxylated oxides.

The macromolecules can be applied before or after the interior functionalization. Moreover, the macromolecules may but do not need to carry the final exterior functionality. The macromolecules can bring general functional groups subject to further chemical reaction that subsequently confers the desired property selectively on the exterior surfaces.

When the pore surfaces are functionalized first, the macromolecules "cover" the exterior non-pore surface and either react with or simply mechanically or electrostatically block the original surface functionalization by making those moieties inaccessible to a subsequent analyte. For example, a negatively-charged polyelectrolyte too large to penetrate the pores can be contacted with particles prefunctionalized with positive moieties such as amine groups. In this example, pores would have a positively-charged surface character while the exterior non-pore surface would have a negatively-charged surface character. Thus, these materials could be used in applications where it is desirable to remove small, negatively-charged molecules from an analyte while retaining large negatively-charged molecules in solution. PCR cleanup is an example of such an application where dNTP and single-stranded primers can be adsorbed on pore surfaces having a positively-charged surface character while large, double-stranded DNA molecules remain in solution.

Alternatively, macromolecules can also first and subsequently functionalize the pores. This strategy is effective to the extent that the macromolecules effectively cover the exterior non-pore surface and block the functionalization chemistry being applied to the pore surfaces. As another alternative strategy, the non-pore functionalization can be chemistry occur "underneath" the macromolecules on the exterior non-pore surface such that the functionality being given to the interior pore surface is "hidden" on the exterior non-pore surface in spite of pore chemistry that also occurs on the exterior as in the example above where the macromolecules are applied after pore functionalization.

In general, surface functionalization as used in the present invention can be carried out using any reaction, method, etc. which results in the desired compound being immobilized on the surface of the nanoporous material. For example, compounds can be immobilized on the surface of the nanoporous material via covalent bond(s) between the compound and surface. Compounds can also be deposited electrostatically onto suitable coatings. When only exterior functionalization is intended, the desired moieties can be pre-attached to the large molecular weight polymer that is electrostatically adsorbed onto the surface. As an example, we could decorate high molecular weight PAA with biotin and then deposit it onto the exterior surfaces carrying the biotin with it and thereby selectively biotinylate the exterior.

For example, positive charge functionality can be introduced by using silanization chemistry (e.g., reaction with amino-silanes such as APTMS) or self-assembly of positively charged polyelectrolytes with low molecular weight (e.g. poly(allylamine), poly(ethyleneimine) or poly(lysine)).

An example of the use of silanization chemistry to functionalize the pore surface of nanoporous silica with positively-charged groups is covalent attachment of amines with aminopropyltrimethoxysilane (APTMS) or any of the commercially available silanes. As another example, exposure of the nanoporous material to small polyelectrolytes, such as low molecular weight polyethyleneimine (PEI), polyallylamine hydrochloride (PAH) or polylysine, which are known to adsorb on native silica. Such functionalization of the pore surface will convey positive character to this surface due to the amine groups which are exposed on the surface. Other types of substrates can be functionalized with analogous surface chemistry. For example, porous alumina can be modified to present the desired chemical groups via phosphonate chemistry and porous titania can also be functionalized with standard silanization chemistry used on silica.

As another example, the pore surface can be functionalized using silanization chemistry (using, for example, commercially available compounds) to attach common hydrophobic groups (such as, for example, alkanes, phenyl groups and fluorinated hydrocarbons).

In another embodiment, the method for preparing a differentially functionalized nanoporous material comprises as an initial step of contacting the nanoporous material with a pore functionalizing material which results in both surfaces being functionalized with the pore functionalizing material. A subsequent step involves contacting the nanoporous material (functionalized with the pore functionalizing material) with a surface functionalizing material which results in the external surface and not the pore surface being functionalized with the external surface functionalizing material. One having skill in the art would recognize other methodologies that would result in the materials of the present invention comprising two distinct functionalized surfaces with the desired properties can be used.

As an example of this embodiment, a nanoporous materials with an adsorption resistant pore surface and a different non-pore surface functionalization on silica particles is produced.

First, a surface is functionalized by silanization with an amine such that a positively-charged surface results. Next, the exterior amines are covered and/or reacted with high MW PAA. Third, the interior amines are reacted with carboxylated oligoethylene glycol of MW such that it can penetrate the pores. This would produce a nanoporous material with an adsorption resistant pore surface and negatively-charged non-pore surface. The non-pore surface could be rendered hydrophobic by using a PAA/hydrophobic copolymer or render it positive by overcoating PAA with high MW PAH. Other orders of application and using mixed silanization layers to impart attachment sites along with adsorption resistant interiors are also possible.

In yet another embodiment, it is possible to selectively remove (or hide) the amines on the exterior non-pore surface by application of a macromolecule. For example, if it is desired that the exterior surface have a negative character, the exterior surface can be last functionalized with, for example, a negative polyelectrolyte such as polyacrylic acid (PAA) with high enough molecular weight (MW) (i.e., large enough size) that the pores remain unaffected. The carboxylate groups carried by the PAA are electrostatically attracted to the amines and since PAA carries them in excess, the exterior charge would be switched to negative. Other negatively charged polymers such as sulfonated polystyrene (SPS) could also be used for this purpose. Note that polyelectrolyte charge and amine charge depend on pH so that this attraction is only in certain pH ranges (in these cases, quite broad from about pH 5 to pH 8). It is also possible to make the coupling pH independent by covalently attaching PAA to the surface amines via carboxylate-amine coupling chemistry.

Functionalization of the exterior can be done in at least two ways. First, mixed silanization layers with a minority component containing marginally hydrophilic groups that carries functional moieties which can be reacted with high MW polymers on the exterior. For example, the nanoporous materials can be functionalized with mixed layers of OTS and a long chain hydrocarbon having an amine termination. The latter will react with carboxylated materials such as PAA and copolymers of PAA with other polymers that are or contain functional units. Reaction with PAA would render the exterior negative while reaction with carboxylated PEG would render it adsorption resistant. Similarly, deposition of positively charged polyelectrolytes such as high MW PAH or PEI on top of PAA could be used to render the exterior positive.

If it is desirable to render the exterior surface hydrophobic, there are at least two general ways to do this. First, we could react a high MW polymer with the surface amines (e.g., a copolymer of PAA with polyethylene) to bring hydrophobic alkanes or other groups to the surface. Second, we could react away excess carboxylate groups on the PAA with amine-containing hydrophobic compounds such as octadecylamine. In the latter case, we can even change exterior surface properties selectively with small molecules since these would not be able to attach to the amine or residual OH groups on the interior of functionalized porous silica. The chemistry to modify some of the PAA carboxylates could be done before or after application of the PAA.

Similar strategies using these two alternatives (prior attachment of the desired functionality to the polymer containing carboxylate or reactions with excess PAA carboxylates not tied up by amines after deposition) can also be used to confer adsorption resistant character to the exterior. For example, high MW carboxylated polyethyleneglycol (COOH-PEG), which cannot penetrate the pores, can be reacted with the amines. Functionalization of a surface with PEG results in a biocompatible, hydrophilic, and adsorption resistant surfaces. Alternatively, aminated oligoethylene glycol can be reacted with excess carboxylate groups to functionalize the surface.

In one embodiment, porous silica microparticles can be functionalized with low molecular weight (MW) polyelectrolytes or APTMS in the pores and with high MW PAA on the exterior using standard techniques.

In yet another aspect, the present invention provides a method for separating double-stranded nucleic acids from single-stranded and/or free (individual) nucleic acids using the nanoporous materials described herein.

In one embodiment, the present invention provides a method for purification of dsDNA from a mixture comprising dsDNA and one or more of dNTPs, primers and/or other ssDNA. The method comprises combining the mixture with the nanoporous material described above, incubating the combined mixture for a period of time to effect sequestration of dNTPs and ssDNA (including primers) on or within the pores of the nanoporous materials; and, separating the nanoporous material from the mixture solution to obtain a purified dsDNA solution. Thus, separating the nanoporous material from the mixture removes dNTPs and ssDNA adsorbed to the nanopore surfaces (and thus, sequestered or trapped in the pores) from the dsDNA which can be recovered in the solution. For example, this method can be used to "clean-up"/ purify a PCR product. On exposure of a PCR product mixture of double-stranded DNA, nucleic acids and dNTP to a nanoporous material of the present invention the double-stranded DNA will not adsorb on the surfaces while other components will adsorb preferentially. The solution removed from the surfaces will be purified double-stranded DNA. FIGS. 1(a) and (b) graphically illustrate typical materials preparation and depict the behavior of a PCR product.

In this embodiment, the pore surface should be functionalized such that it strongly adsorbs dNTP and single strands of nucleic acids while the exterior non-pore surface of the nanoporous material should be resistant to double-stranded nucleic acid adsorption. One strategy is to functionalize the pores to present positive charge while functionalizing the exterior to present either negative charge or completely inert (i.e., adsorption resistant) surfaces that inhibit amplicon adsorption. The positive charge could be introduced onto porous silica particles using either silanization chemistry (e.g., reaction with amino-silanes such as aminopropyltrimethoxysilane) or self-assembly of positively charged polyelectrolytes with low molecular weight (e.g., poly allylamine, polyethyleneimine or polylysine). Since these would presumably coat both interior and exterior surfaces, we would block the exterior surfaces with large negatively charged polyelectrolytes (such as high molecular weight poly acrylic acid) too large to penetrate into the pores. It may also be possible to use hydrophobic coatings in the interior and hydrophilic, negative or inert coatings on the outside of the particles to differentially adsorb dNTP and primers.

The present method is unlike previous methods where all the components of an amplification reaction are mobilized on homogenous surfaces and various components are then selectively eluted. The method provides a single step separation methodology combining size-exclusion (e.g., materials with a hydrodynamic radius greater than the average pore size of nanoporous material is excluded) with surfaces having differential absorption characteristics such that a subset of small molecules and complexes can be selectively removed from mixtures for purification or assay applications.

The mixture comprising dsDNA and nanoporous material can be incubated for periods of time ranging from less than one minute to several minutes. The incubation time can be optimized by one skilled in the art to account for various nucleic acid amplification reaction parameters, such as the volume of the mixture that is combined with the nanoporous material, as well as the amount of dsDNA, ssDNA and/or dNTPs present or expected to be present in the mixture. For example, and without intending to be bound by any particular theory, it is generally considered that between 40-200 uM dNTP is an optimal dNTP concentration for conventional PCR reactions. Likewise, it is generally considered that between 0.1-1.0 uM is an optimal concentration of PCR primers for typical PCR reactions. However, greater or lesser concentrations of dNTP and/or primers may be used for certain amplification reactions, depending on a variety of factors, such as the amount and quality of DNA template, the length of expected amplicons, and the number, timing and temperatures of amplification cycles. Therefore, the incubation period can be extended or shortened for any particular PCR protocol so as to optimize the amount of time unincorporated dNTPs and/or unincorporated primers have to diffuse into the nanopores. The invention contemplates incubation times of more than one minute, and times between 5-60 seconds inclusive, and including all integers between 5 and 60 seconds. Further, the incubation period can be adjusted to achieve a desired amount of dNTP or ssDNA removal, and/or a desired amount of dsDNA retention in the mixture. For example, in one embodiment, an incubation period of between 30 and 45 seconds is sufficient to remove greater than 90% of the dNTPs and maintain greater than 80% of PCR amplicons in the mixture solution.

The amount of inhomogenously functionalized nanoporous material added to a particular nucleic acid amplification mixture can be optimized by taking into account a variety of factors. For example, and without intending to be bound by theory, it is possible to calculate the moles of dNTPs and primers that are added to a particular nucleic acid amplification reaction. It is also possible to estimate, based upon factors such as the number and temperature of amplification cycles and expected polymerase activity, the amount of unincorporated dNTP and primers that will remain in the mixture once the amplification protocol is complete. Accordingly, the total capacity of the nanoporous material in the mixture to adsorb unincorporated dNTP and primers can be adjusted to provide more (or less) nanopore surface area to facilitate removal of as much dNTP and primers as possible, without causing the mixture to become difficult to process because of, for example, increased viscosity. For instance, in a typical PCR reaction volume of 100 uL that comprises at the start of the amplification protocol a conventional concentration of dNTPs and primers, an exemplary amount of the nanoporous material that could be added to the solution post-amplification to remove unincorporated dNTP and primers is between 2-4 mg.

The nanoporous material (with the trapped contaminants) can be separated from the dsDNA by a suitable technique, including but not limited to spinning and magnetic techniques. Alternatively, the nanoporous material may be retained by filtration and removal of the amplification solution, such as by pipetting. This will result in separation of dsDNA from the contaminants thereby providing a purified double-stranded nucleic acid solution. The amount of contaminants remaining in (or removed from) a purified double-stranded nucleic acid preparation can be determined by standard techniques such as spectroscopic analysis.

It is expected the invention can be used to purify double-stranded nucleic acids to any desired degree of purification, such as partial purification, substantially complete purification, or complete purification. In different embodiments, the contaminants may comprise less than 50%, less than 40%, less than 30%, less than 20%, less than 10%, less than 5%, or less than 1%, and less than all integers in between 50% and 1%. The invention may also result in a double-stranded nucleic acid preparation that is completely free from contaminants. Thus, the double-stranded nucleic acids may comprise 50% to 100%, including all digits there between, of the nucleic acids in the solution after the porous nanoparticles are separated from the mixture.

The method of the present invention can be used for purifying dsDNA from a nucleic acid amplification reaction solution, a concentrated DNA plasmid preparation, a restriction digest preparation, a DNA extraction, test hybridization solutions of DNA and/or RNA, an RNA preparation, or a ssDNA site-directed mutagenesis reaction, and the like. The double-stranded nucleic acids purified using the method of the invention can be double-stranded DNA, double-stranded RNA, or single-stranded (ss) nucleic acid molecules that adopt significant regions of double-stranded structure. The double-stranded nucleic acid molecules can be linear or circular. Using the method and nanoporous materials of the present invention, dsDNA of as few as 10 by can be isolated from an amplification reaction.

In one embodiment, porous silica microparticles with pore surfaces functionalized with APTMS and non-pore surfaces functionalized with high MW PAA are used in the method. Several mg of nanoporous material is added to 100 uL of an aqueous solution of ss/ds DNA mixtures and on separation of the nanoporous material and mixture only ds DNA is retained in the aqueous solution.

In another embodiment, porous silica microparticles with pore surfaces functionalized with positively-charged low MW polyelectrolytes and non-pore surfaces coated with high MW PAA. Several mg of nanoporous material is added to 100 uL of an aqueous solution of ss/ds DNA mixtures and on separation of the nanoporous material and mixture only ds DNA is retained in the aqueous solution.

In other aspects, the present invention provides methods for separating double stranded nucleic acids from proteins. Non-limiting examples of the proteins include enzymatic proteins, such as polymerases and nucleases. The polymerases include without limitation DNA polymerases, RNA polymerases, reverse transcriptases, and RNA-dependent RNA polymerases. The nucleases include without limitation restriction endonucleases, and DNAse and RNAse of all varieties.

In various illustrative embodiments, for some downstream applications of amplified DNA, it is desirable to separate the ds DNA from the DNA polymerase enzyme used for DNA amplification, such as Taq polymerase However, because DNA polymerases are negatively charged and have large molecular weights and therefore would likely not penetrate the pores of the heterogeneously functionalized nanoparticles disclosed herein, the present invention provides for the use of nanoporous particles having hydrophobic surface functionalization to selective adsorb the polymerases and/or other proteins that may be present with double stranded nucleic acids in a mixture. In this regard, we demonstrate separation of Taq polymerase from ds nucleic acid using nanoporous particles functionalized with hydrophobic moieties. It is expected that this result can be extended to separation of double stranded nucleic acids from other proteins, such as enzymes involved in nucleic acid catalysis, since it is known in the art that, for example, nucleases will selectively adsorb onto hydrophobic surfaces while double-stranded DNA does not. It is also known that whether any particular protein will adsorb onto a hydrophobic surface is correlated with the aromatic amino acid content of the protein, and that those proteins having greater than 10% aromatic amino acid content will have high affinity for hydrophobic surfaces. (See, for example, Cashion et al., Nucleic Acids Research, vol. 8, No. 5, Mar. 11, 1980, pp. 1167-1185.)

In one embodiment, a nanoporous silica partially covalently functionalized with OTS (octadecyltrichlorosilane) such that the non-pore surface is hydrophobic can be used to remove Taq polymerase from solution. The degree of OTS coating is such that the particles remain hydrophilic and easily dispersed in water.

Alternatively, nanoporous materials comprising a non-porous surface fictionalized with a polyelectrolyte compound having multiple functionality (i.e., different functional groups) can be used to selectively remove polymerase. For example, copolymers of PAA and a hydrophobic moiety such as polyethylene can be used to functionalize the non-pore surface. This functionalized surface will be rendered unattractive to large ds-DNA due to the fact that the PAA electrostatically resists DNA adsorption, but the hydrophobic regions will remove polymerase because it is much more hydrophobic than ds-DNA. The degree of hydrophobicity of the non-pore surface can be tailored appropriately by using different copolymers with varying functional group composition. The multiple non-pore surface functionality can also be created by substitution of a controlled number of the carboxylate groups on the PAA with hydrophobic groups. For example, PAA can be reacted with an appropriate amount of octadecylamine prior to or after functionalization of the non-pore surface.

The separation of ds nucleic acids from proteins with hydrophobic character can be accomplished as part of a one-step cleanup of PCR solutions. Protein removal may comprise using more than one nanoporous material (e.g., mixed beads)

In another embodiment, nanoporous particles can comprise non-pore functionalization(s) so as to have both negative charge and hydrophobic character, which would permit, for example, PCR cleanup and enzyme removal simultaneously with a single nanoporous material, e.g., nanoporous beads. In one embodiment, a non-pore surface is functionalized with copolymers of PAA (for example where the copolymer is hydrophobic (e.g. polyethylene or polystyrene)).

Yet another embodiment of the invention is directed to cleanup of labeling reactions. It is frequently desirable to add fluorescent or other tags (e.g, biotin or ferrocene) to oligonucleotides. Following these reactions, unattached fluorescent dye must be removed from the mixture to purify the tagged oligonucleotide. The general methodology of the methods described herein can be applied to these situations where it is desirable to adsorb the tags in the pores of the nanoporous material while excluding the oligonucleotides. A nanoporous material with very small pores (down to 30 A are commercially available in silica) functionalized such that the free label is adsorbed in the pore and the tagged single strand cannot enter the pore can be used. Pore surface functionalization rendering the pore surface positively-charged, negatively-charged or hydrophobic can be used depending on the nature of the label.

Still another method is directed to hybridization assay applications. Hybridization assays are done for sequence testing in DNA or RNA (e.g., rapid SNP detection in PCR amplified genomic DNA). Hybridization assays are common, for example, in genetic screening technology. In general, following chemical amplification of DNA, rapid tests to determine whether the correct target sequence was amplified are valuable. Often, gel electrophoresis is used to assess whether fragments of the expected length have been amplified but gel electrophoresis is slow and cannot be easily used for detection of single nucleotide polymorphisms (SNPs). A common alternative, at least for DNA, is real-time PCR where probes are incorporated into the amplification process to do specific sequence detection. The hybridization assay herein obviates the need for the complex assay design and infrastructure needed for real time PCR and enables the use of simple PCR followed by a rapid hybridization assay with a tagged probe to accomplish the same purpose. Because we can differentially adsorb and remove single-stranded DNA while leaving a preponderance of double-stranded (or partially double-stranded) DNA in solution, we are able to assess whether tagged, single-stranded probes have hybridized with target sequences. These targets can be single-stranded complements (or partial complements) or can be double-stranded DNA where the single-stranded probes bind with one strand of the duplex following a dehybridization and annealing step. The targets can also be partially duplex structures where the probe oligonucleotide binds to single-stranded regions on the target as might be the case for binding to folded RNA or for sandwich assays.

The particles for differential adsorption could be composed of silica, alumina, titania or possibly hydrophilic water soluble polymers. Porous particles have the advantage of having increased adsorption area. Since the particles will be treated with hydrophobic coatings but it is advantageous to have water-soluble particles, there may also be some advantage to porosity in allowing for large surface area that is relatively difficult to turn hydrophobic. The hydrophobic coatings will typically be covalently bound to the particle surface, as for example using silanization chemistry to modify or partially modify the silica surface with hydrophobic moieties such as alkanes or phenyl rings. Without intending to be bound by any particular theory, it is considered that the physical reason why hydrophobic surfaces can differentially adsorb single-stranded DNA is that it is much more hydrophobic than double-stranded DNA. The thermodynamics driving the adsorption is that relatively hydrophobic entities can adsorb and replace water forced to reside at hydrophobic surfaces where it cannot effectively satisfy its bonding requirements. The release of the interfacial water leads to an entropic gain that makes the adsorption thermodynamically favorable. The invention contemplates addition of chaotropic salts to tune this process and increase contrast between the adsorption efficiencies of the relevant species.

A non-limiting illustration of a protocol useful for performing hybridization assays according the invention is as follows.

First, tagged probes are added to a DNA sample to be assayed. The probes can be single-stranded oligonucleotides that have minimal or no secondary structures. The tags can be fluorescent dyes (e.g. rhodamine, fluorescein, cy-3, cy-5, etc.), redox moieties (e.g. ferrocene, etc.) or radioactive labels (e.g. $^{32}P$). The targets can be any nucleic acids. Non-limiting examples include double-stranded genomic DNA, PCR amplified DNA, duplex-containing RNA or DNA, or unlabeled single strands of DNA or RNA. For PCR amplicon targets the tags can be added to the PCR mixture before amplification since they are typically short compared to primers and will not interfere in the PCR. This avoids additional handling and potential contamination. For example, typical primers have 20-25 bases and a $T_m$ of about 55° C., thus probes with about 15 bases having a $T_m$ of about 40° C. will only anneal on the last cycling step when the sample is finally cooled below 55° C.

The second step comprises heating the mixture to allow the probes to hybridize with the target. When the target is double stranded, it is necessary to dehybridize it so that the probes can hybridize with the target. In the case of PCR amplification, hybridization of the probes is performed as the last step of the thermal cycling protocol, which typically comprises heating the system to 95 degrees and cooling to below the melting temperature of the probe-target complex (e.g. ~40 degrees Centigrade for a 15-mer probe). This hybridization assay protocol could be used with DNA or RNA amplification methods other than PCR to assess whether a particular target is present. These other methods include but are not limited to ligase chain reaction, transcription mediated amplification, strand displacement amplification and isothermal amplification. In the case of single nucleotide polymorphism (SNP) detection, the hybridization solution is annealed under stringency conditions (usually a temperature in between melting temperatures of wild-type and mutant probes) where determination of single base mismatches is feasible. However, the assay is independent of the hybridization and can be run under ambient conditions.

Third, the annealed mixture is exposed to the particles with hydrophobic coating. The particles can be comprised of silica, titania, alumina, etc. and are functionalized with a hydrophobic layer such as alkanes attached to silica via silanization chemistry. It may be advantageous to incompletely functionalize the nanoporous particle surfaces so that they retain enough hydrophilic character to disperse well in aqueous solution. The porous particles take advantage of high surface area for adsorption. The exposure can be via adding a dispersion of beads to the analyte or vice versa. Alternatively, the particles can be in dry form and contained in a tube or pipette. The analyte can be added to the tube or aspirated into the pipette. During the exposure, unhybridized single strands will adsorb on the beads. Thus, separation of the beads from the analyte (or vice versa) will leave only probes that have hybridized with the target in solution.

Finally, the solution is assayed for the presence of the tag. For example, fluorescent tags are detected using photoluminescence and redox tags using cyclic voltammetry or differential pulse voltammetry. Its presence indicates successful hybridization of the probe with the target and, hence, the presence of the complementary sequence in the target.

Figure 1B:
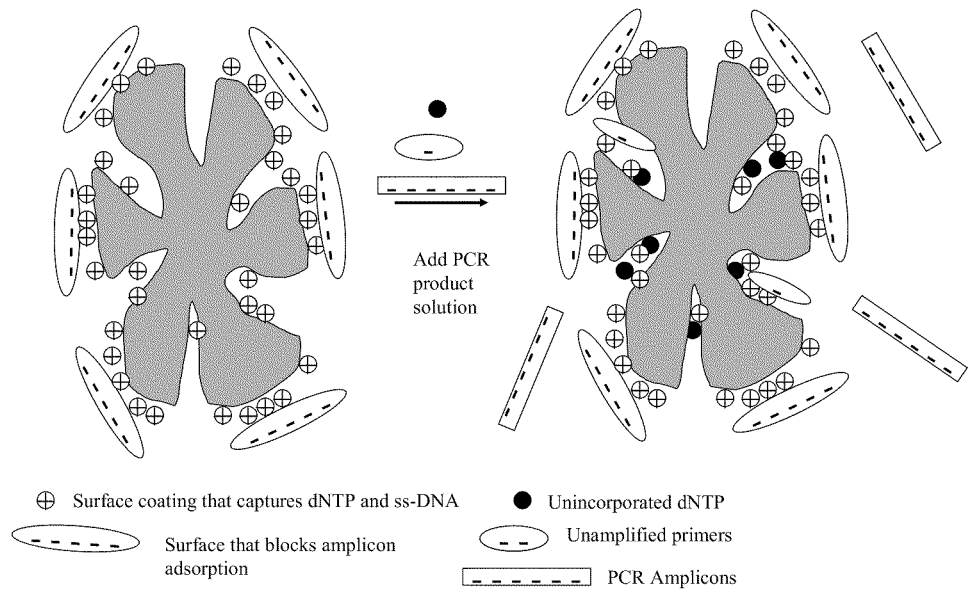
FIG. 1(b). Graphical depiction depicting how contaminants be removed from mixtures by exploiting differential functionalization of interior and exterior surfaces.

In another embodiment, in order to determine whether a probe oligonucleotide with a label has hybridized with its complementary sequence on genomic or PCR amplified DNA or RNA, the probe can comprise a sequence matching the target amplicon that has been deliberately included in the PCR reaction but with melting temperature lower than that of the primers so it does not interfere with PCR. In this case, nonporous materials of the present invention, e.g., the nanoparticles in FIG. 1(b), can be added to the final mixture. If the probe hybridizes with the amplicon on cooling below its melting temperature, it will not be adsorbed since the resulting complex is too large to penetrate the pores of the nanoporous material. If the probe does not hybridize with the target, it will be adsorbed in the pores of the nanoporous material. Therefore, the presence of labels in the analyte (determined by, e.g., fluorescence or redox techniques) once the nanoporous material is removed demonstrates the presence of target sequence. Additionally, the method can be adapted to use colorimetric assays to demonstrate the presence of the target hybrid based on salt-induced aggregation of colloidal gold nanoparticles.

Other hybridization examples include the following. Removal of unhybridized tagged oligonucleotide, where the unhybridized tagged oligonucleotide an unextended primer. In this embodiment, lack of tag signal in the analyte remaining after removal of single strands would reflect failed PCR amplification. Conversely, the presence of tag signal would indicate that the primers had been extended and that PCR worked. This latter circumstance reflects the presence of target sequence in the original sample Use of several oligo sequences with different dye tags simultaneously to detect multiple targets (for example, for readout of multiplex PCR or for SNP genotyping where one probe would be wild type complement with one type of fluorophore and the other the mutant complement sequence with a distinguishable fluorophore). A suitable stringency test as described above is preferred in the SNP case. A special case for SNP detection would combine the use of several oligo sequences with different dye tags simultaneously to detect multiple targets and removal of unextended primer where two primers overlapping the SNP with wild-type and mutant sequences having distinct tags are used and the amplified PCR solution is exposed to the hydrophobic medium to remove unextended primers. In this case, the stringency test would be integrated into the PCR thermal cycling protocol by adjusting the primer annealing temperature to prefer the perfectly complementary primer(s).

Another use includes the deliberate addition of salts to facilitate differential adsorption and optimize ss versus ds contrast. Because fluorescence is sufficiently sensitive, a small aliquot of the hybridization solution can be greatly diluted in other buffer solutions and allow us to control the strength of the hydrophobic effect during exposure to the coated particles.

Yet another use includes use of additional mixed surface functionalization, such as, for example, including a low density of FRET quenchers which would not alter the hydrophobic character but would serve to quench the fluorescence of tagged single strands that do not hybridize and thus obviate the need to remove the beads prior to reading fluorescence. Examples of FRET quenchers includes, but are not limited to, BHQ™ (Biosearch Technologies) and Iowa Black™ (Integrated DNA Technologies) and Blackberry650™ (Berry Associates). These materials can be covalently attached to mixed silanization layers. We expect 0.001-0.1 monolayers of quencher to be adequate to provide nearly complete quenching based on typically Förster energy transfer radii.

In the case where electrochemical essay is used, the nanoporous materials it may not be necessary to remove beads for electrochemical assay because adsorbed redox tags will have dramatically reduced diffusivity and therefore, the signal they contribute to voltammetry will be commensurately reduced.

Still another example includes insertion of tagged ss probes into triplexes (where it is expected the triplex not to adsorb).

The following Examples are presented to illustrate the present invention. They are not intended to limiting in any manner.

EXAMPLE 1

Example of differentially functionalized nanoporous material prepared by covalent attachment of non-pore functionalization.

Mesoporous silica, chromatography grade silica, Merck 9385, is one-example of suitable substrate for use in the invention. This silica is typically spherical, with a diameter of 40-60 microns, pore size of 60 Å and a BET surface area of 480-540 m2/g. The nanopores and surface can be functionalized with amine groups by grafting with APTMS. For this Example, APTMS (Fluka), 0.5 mL, was added to 25 mL of EtOH and the solution was stirred for 5 minutes in a 100 mL round bottom flask. Merck 9385 silica gel, 1 g, was added to the solution, and the slurry was refluxed for 1 hour. The slurry was transferred to a 100 mL beaker and the solution decanted. The silica was washed with 200 mL of hot water in 8 aliquots, by stirring and decanting. Finally, the silica was washed with 25 mL of room temperature water, and dried in an oven at 110° C. for 30 minutes. This procedure is believed to result in APTMS functionalization on all hydroxylated silica surfaces, internal and external.

The silica particle surface, but for the nanopores, was then functionalized with carboxylate by the introduction of poly(acrylic acid sodium salt) (PAA), which self assembles only at the particle surface because it is too large to enter the pores. Evidence for this is provided both by functional assays and FTIR spectroscopy data presented below. Poly(acrylic acid sodium salt), 100,000 MW (Aldrich) was added to the external surfaces as follows. APTMS functionalized gel, 0.5 g, was added to 10 mL of PAA solution (0.01M in PAA, 0.1M in NaCl). The slurry was mixed on a rocker for 20 minutes. The gel was washed by successive centrifuging and decanting three times with 10 mL of water each, followed by a final wash with 10 mL of EtOH. The gel was dried in an oven at 110° C. for 10 minutes.

1. Verification of the Surface Chemistry

Figure 2:
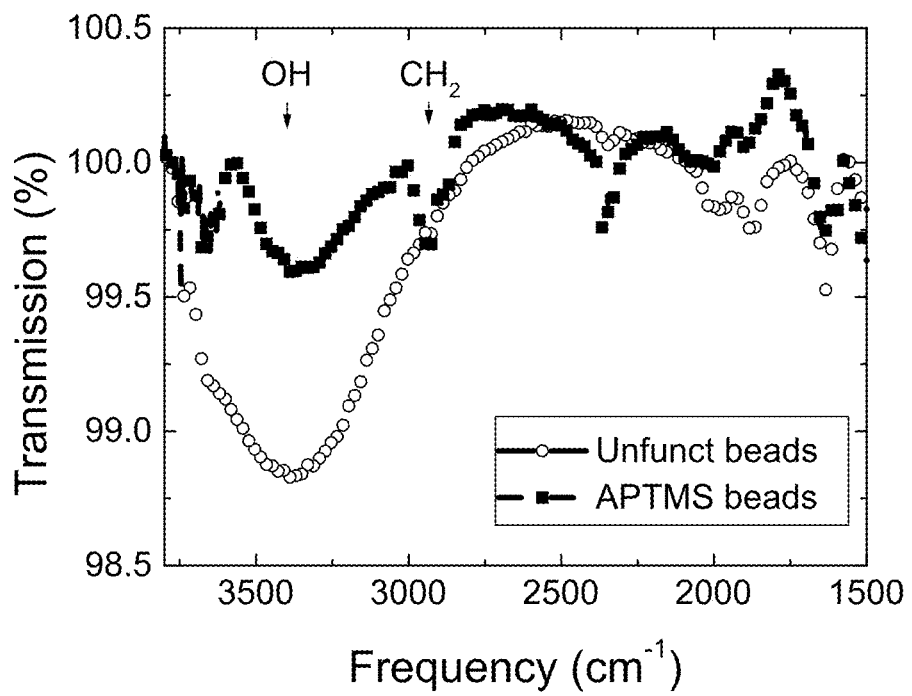
FIG. 2. FTIR spectra of unfunctionalized porous silica (solid black) and aminopropyltrimethoxysilane (APTMS) modified porous silica (dashed). The OH and $CH_2$ stretching vibrations are labeled and assignment of other bands are discussed in Example 1.

We used Fourier Transform infrared spectroscopy (FTIR) as an analytical approach due to its simplicity, broad availability and ability to provide us with molecularly specific information. To the extent that infrared mode absorption cross-sections are known, we can also compute approximate surface coverage of various moieties. FIG. 2 presents the FTIR spectra of the porous silica beads untreated and treated with APTMS. In each case, the beads are dispersed into a KBr pellet whose transmission is measured with a Shimadzu 8400 FTIR spectrometer.

Assignment of the spectral bands using spectra of pure APTMS is straightforward. The broad absorption on untreated beads near 3400 cm$^{-1}$ is due to hydrogen-bonded surface OH groups while the absorption at 1635 cm$^{-1}$ is from the silane bound OH bend and the 1100-1200 cm$^{-1}$ band (not shown) is from the Si—O stretching vibrations in the bulk. This latter band serves as an excellent reference to correct for the total amount of material. The band near 2300 cm$^{-1}$ is due to $CO_2$ in the atmosphere uncorrected for by background subtraction since the quality of the spectrometer purge varies with time. The silanization attachment chemistry removes a substantial portion of the OH band intensity and while clear new bands in the $CH_2$ stretching region associated with APTMS appear. The substantial suppression of the OH stretch not only indicates effective attachment of APTMS to the treated surface but also proves that APTMS effectively infiltrates the pores. Since the vast majority of total surface area is in the pores (only approximately 0.2% of the total surface area is on the exterior), the substantial reduction of surface OH means that much of the surface has been chemically modified. A rough estimate of the amount of adsorbed APTMS can be obtained from the strength of the $CH_2$ stretching absorption and is consistent with substantial (>10%) coverage of the total surface area of the bead. The small amount of PAA signal is attributable to the fact that its large molecular weight prevents it from entering the pores and adsorbing on the vast majority of bead surface area. We know that PAA is present from the fact that beads treated with only APTMS efficiently remove DNA amplicons from solution.

We used Fourier Transform infrared spectroscopy (FTIR) as an analytical approach due to its simplicity, broad availability and ability to provide us with molecularly specific information. To the extent that infrared mode absorption cross-sections are known, we can also compute approximate surface coverages of various moieties. The silanization attachment chemistry removes a substantial portion of the OH band intensity and while clear new bands in the $CH_2$ stretching region associated with APTMS appear. The substantial suppression of the OH stretch not only indicates effective attachment of APTMS to the treated surface but also proves that APTMS effectively infiltrates the pores. Since the vast majority of total surface area is in the pores (only approximately 0.2% of the total surface area is on the exterior), the substantial reduction of surface OH means that much of the surface has been chemically modified. A rough estimate of the amount of adsorbed APTMS can be obtained from the strength of the $CH_2$ stretching absorption and is consistent with substantial (>10%) coverage of the total surface area of the bead. Our FTIR instrument is not sensitive enough to see PAA overlayers on the particles but we have verified their deposition independently using confocal microscopy with fluorescently modified PAA. There, it is possible to determine that the PAA adsorption is almost exclusively on the particle exteriors since we can image using depth of fields (~1 micron) much smaller than the particle sizes (~50 microns).

2. Cleanup Efficacy a. Throughput of PCR Solution Components

Initial studies to determine the efficacy of the beads in removing the various components of PCR product solution were done using a NanoDrop 1000 absorption spectrometer. The NanoDrop data provide quantitative information on the amount of interaction between the individual PCR solution components and the functionalized beads. We measured the amount of purified PCR amplicons, ss-DNA (TAATACGACTCACTATAGGG; SEQ ID NO:1), annealed self-complementary ss-DNA (ATCGTCCTGCAGGACGAT; SEQ ID NO:2) and each dNTP (dATP, dCTP, dGTP and dTTP) retained in solution after ~30 second exposure to the differentially functionalized beads described above. The PCR amplicons were 530 bp, 1063 by and 1956 by bands from a New England Biolabs (NEB) Lambda DNA template (NEB N3011S) amplified using our designed primers 11F (TGA AAC GCT TGC TGC AAC GCC AAA; SEQ ID NO:3) and 15R (AAA GCA ATT GGC GGT GAT GTA AAC ACT ATG; SEQ ID NO:4) with reagents and reaction conditions from NEB (E5100S), a 60 deg C. annealing temperature, a 2.5 minute extension time, and 25 cycles. The amplicons were recovered from solution using the Invitrogen PureLink PCR Purification Kit (K3100-01). We used absorbance at 260 nm region as a measure of relative concentration before and after exposure to the beads. In each case, the aforementioned analytes were dissolved in a 20 mM Tris buffer (pH 8.4) with 50 mM $K^+$ and 2 mM $Mg^{2+}$ constituted to simulate the Invitrogen PCR buffer solution and the analyte concentrations were in the neighborhood of what might be expected from PCR product (primer was 10× typical concentration, dNTP was 0.2× typical and amplicons were typical for PCR). The idea behind evaluating Lambda DNA and purified amplicons before and after exposure to the beads was to test dsDNA retention in solution. The synthetic ssDNA sequences were intended to simulate primers while the self-complementary sequences simulate incidental primer dimers. We define the latter as primers that complement either parts of themselves or the other primer such that they might form partial duplexes at 25° C.

Figure 3:
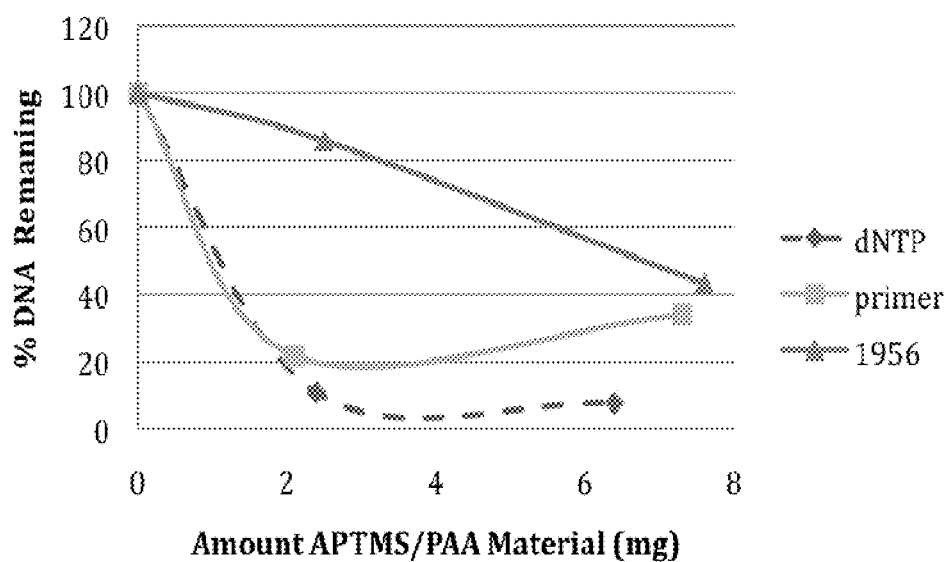
FIG. 3. Graphical representation of retention of model primer, dNTP mixture and a 1956 base pair PCR amplicon versus weight of differentially functionalized porous beads data.

FIG. 3 presents "dosing curves" for both dNTP, primer and dsDNA (1956 by purified PCR amplicons). These quantify the amount of material remaining after 30 second exposure to various numbers of beads. Pure solutions (25 µl) of each were mixed with the beads for 30 seconds and, after a centrifugation step to separate the beads, an aliquot of the supernatant was sampled using a NanoDrop spectrometer that recorded spectra in the 240-280 nm spectral range. Initial concentrations of the primer, dNTP and amplicons were ~3.5 µM, 170 µM and 0.02 µM (23, 56, 14 ng/µL) respectively.

Approximately 2 mg of beads are adequate to remove ~90% of the dNTP or primers at concentrations and amounts typical of PCR product solutions. Even though primers (typically 20 bases) are much larger than dNTP, the surface area demands of the dNTP are far greater since dNTP concentrations are nearly 1 mM while primer concentrations are at most 1 µM. The beads must therefore be able to accommodate as much as ~25 nmoles dNTP (~$1.5 \times 10^{14}$ molecules). A 2 mg quantity of beads carries ~$10^4$ cm$^2$ surface area. If the areal coverage of APTMS is ~10% as estimated above, the result of FIG. 3 can be achieved even if only every hundredth APTMS site adsorbs a single dNTP molecule.

Measurements of the amplicon retention show that solutions after exposure to the beads are slightly more concentrated than prior to the treatment. The reason for this is that the pores retain some water while not allowing amplicons to penetrate. This results in an effective concentration of the amplicons. Total amplicon retention can be quantified in at least two ways. First, we can measure the amount of retained water and correct the concentration reported by the NanoDrop measurement (or, alternatively, recover as much water as possible and redilute with buffer to the original 25 µl volume). Second, we can simply use larger analyte volumes so that the amount of water retention becomes less important. Using either approach, we conclude that recovery of the 1956 base pair amplicons is 85+/−5% (where the quoted uncertainty is derived from the standard deviation of multiple experiments). Thus, choosing a bead quantity of 2 mg for cleanup of 25 µl PCR reactions should give us excellent rejection of dNTP and primers and retention of amplicons. This quantity represents a small fraction of the volume of the solution to be cleaned up.

Figure 4A:
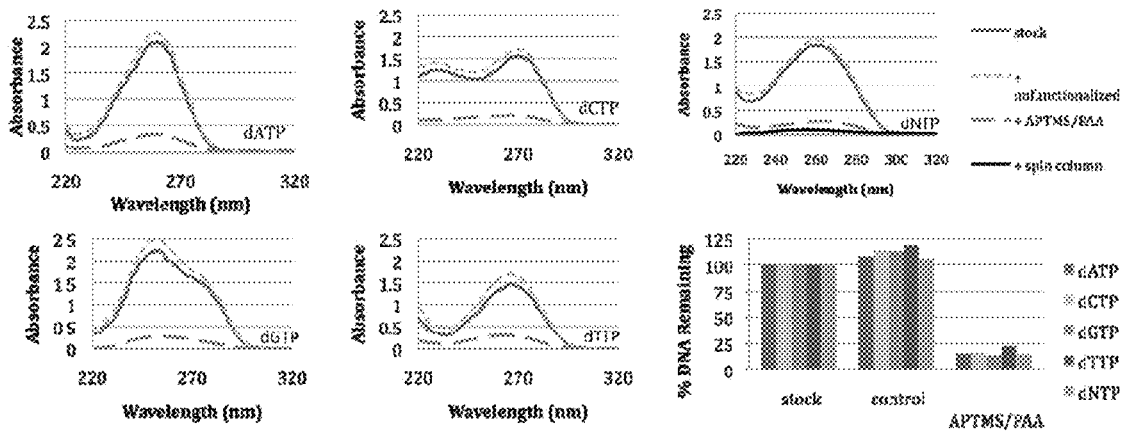
FIG. 4a. Absorption spectra of nucleotides before and after treatment with differentially functionalized porous beads. Solid-line spectra are stock solution spectra and short-dashed-line spectra are taken after treatment using unfunctionalized porous beads. Long-dashed-line spectra are the results after treatment with the APTMS/PAA beads described in text. For the dNTP solution, the dot-dashed line presents the spectrum after treatment with the Invitrogen PureLink PCR Purification (K3100-01) kit.
Figure 4B:
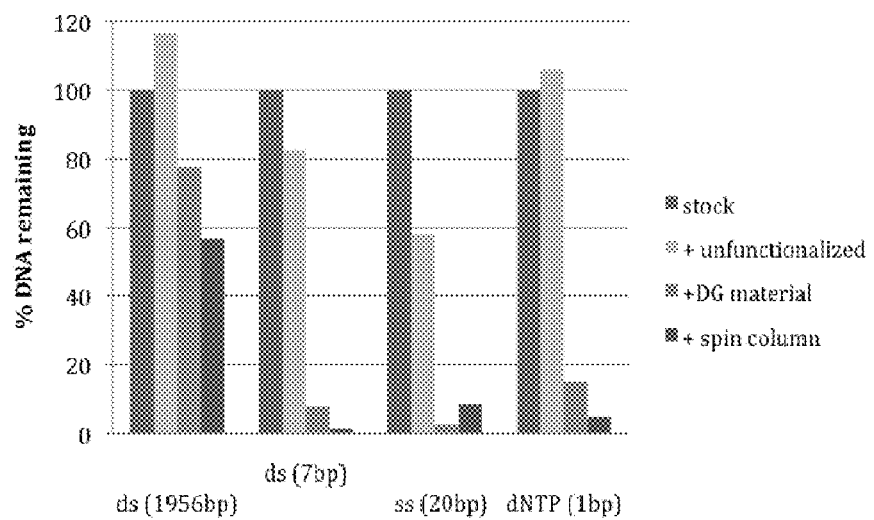
FIG. 4b. Graphical representation of retention of amplicons (1956 bp), "primer dimers" (ds 7 bp), single strands (ss 20 bp) and dNTPs from stock solutions.

FIG. 4a presents the raw data from experiments where the various dNTP components, primers and amplicons are exposed to 2 mg of the APTMS/PAA functionalized beads. In each case, we used 2 mg of beads and 30 second exposure times. Tubes were centrifuged (10,000×g, 10 seconds) to pellet the material and the supernatant concentration was immediately measured on the NanoDrop 1000. FIG. 4b summarizes derives retained fraction from these data and compares it with what was obtained using an Invitrogen PCR purification kit. 15 µl stock was mixed with 2 mg beads for 30 seconds and sampled as in FIG. 4a. Analogous solutions were treated with the Invitrogen PureLink PCR Purification (K3100-01) kit ("spin column"); ds (1956 bp) increases with unfunctionalized beads due to water retention by the beads. Note that we also tested pure polymerase in simulated buffer in like manner and observed complete removal by the functionalized beads. It is likely that positive moieties on the enzyme adhere strongly to the PAA exterior coating.

Figure 5:
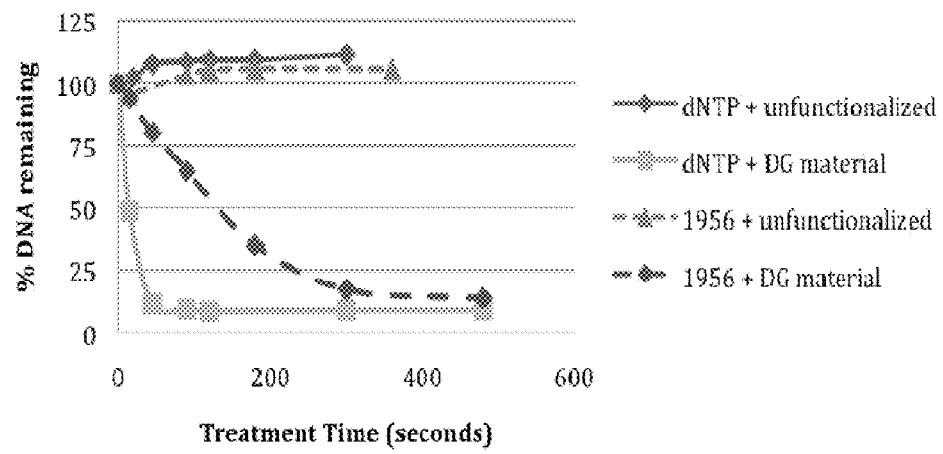
FIG. 5. Graphical representation of kinetics of removing dNTP and amplicons (1956 bp) from solution using treatments by APTMS/PAA functionalized porous beads.

We analyzed the adsorption kinetics to determine how long one should incubate the PCR product with the beads prior to removing it. 25 µl dNTP or amplicon solution was aspirated into a pipette tip containing 3.5 mg material (unfunctionalized, diamonds and triangles or functionalized, squares and circles), mixed, and 1 drop was dispensed onto the NanoDrop spectrometer at the indicated times. For this measurement, we employed a pipette format where we aspirate and eject material. FIG. 5 shows that, in this particular embodiment, optimal times are between 30 and 45 seconds where >90% of the dNTP has been removed and >80% of the amplicons remain. This window is satisfactory to establish a robust protocol but, based on our results presented here, we expect that further optimization of the materials and fluid handling protocol will achieve faster impurity removal and further stabilize the amplicons to remain in solution indefinitely.

b. Throughput for PCR Product

Figure 6:
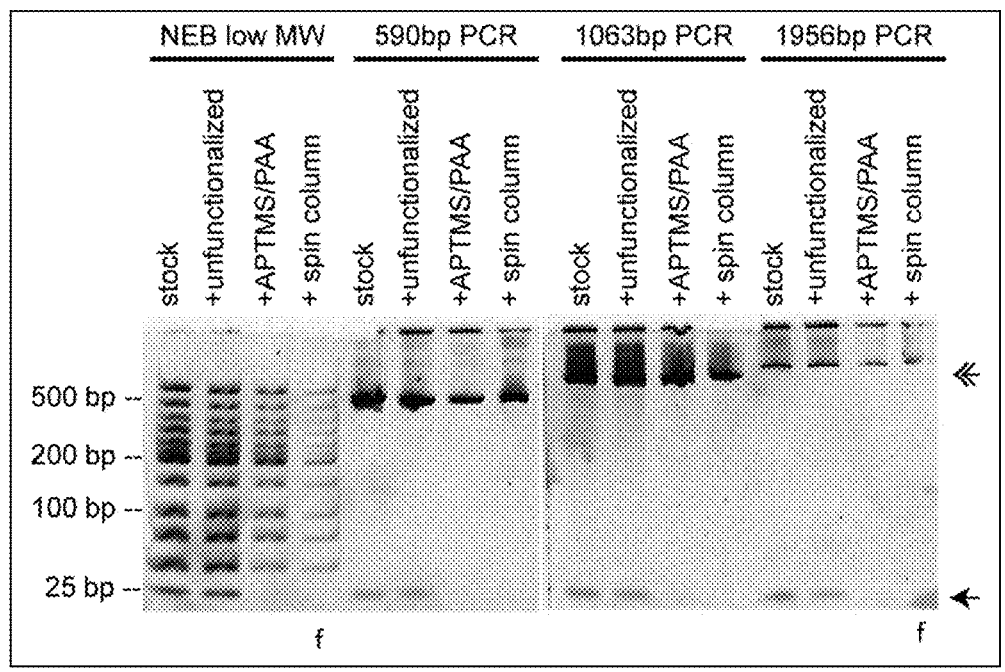
FIG. 6. Gel electrophoresis results for three different PCR products and a reference low molecular weight ladder (NEB N3233S) following treatments with the differentially functionalized porous beads, the Invitrogen PureLink kit ("spin column") or controls.

The testing in the previous section has the advantage of rigor since we worked with dNTP, primers and amplicons independently. Hence, there was no apparent ambiguity in interpretation of UV absorbance even though all three components adsorb in the region between 240 and 280 nm. Nevertheless, we analyzed bona fide PCR product and its attendant complexities. In order to analyze each component independently, we mass separated them with gel electrophoresis (FIG. 6). PCR was run as above except that three different length segments of Lambda DNA (590 bp, 1063 bp, and 1956 bp) were amplified from a lambda template (NEB N2011S) using three sets primers.

All DNA used in the cleanups and controls came from the same PCR tubes and 5 microliters was run on the gel. Stock lanes include unaltered sample for comparison. 15 µl of DNA solution was mixed in tubes containing 2 mg unfunctionalized or functionalized beads for 15 seconds and a 5 microliter aliquot for gel analysis was removed after centrifugation as in FIG. 4. For the spin column control, 50 microliters of each reaction was treated with the Invitrogen PureLink PCR Purification Kit (K3100-01) according to the manufacturer's instructions (with the addition of an extra spin to remove residual wash buffer) and eluted in 50 microliters volume; 5 microliters was run on a 5% polyacrylimide gel. Care was taken to ensure that equal volumes were loaded in each lane. However, lanes denoted by 'f' at the bottom have reduced concentrations due to floating samples most likely caused by residual ethanol from the spin column purification. The residual ethanol persisted despite 3 spins to remove wash buffer (protocol requires 2 spins) and a short incubation at 100 degrees C. The solid arrow points to the single stranded primer bands (~20 bp) while the double arrow indicates the area where the double-stranded amplicons (590, 1063, or 1956 bp) are found.

Qualitatively, the results in FIG. 6 essentially confirm the results of FIG. 4, namely efficient retention of DNA and rejection of primers, comparable to what was achieved with the commercial spin column treatment. It is notable that in FIG. 6, treatment of the low molecular weight ladder standard with our method appears to give substantially better DNA retention in the molecular weight range lower than 500 bp. While most PCR amplification for sequencing involves longer amplicons, this nevertheless suggests a potential area of differential performance advantage for the present invention.

3. Sequencing Following Cleanup

The largest application for cleanup of PCR reactions is use of the amplicons for capillary sequencing, and for this purpose efficient removal of primers and dNTP is critical. We have tested the present invention using exposure to differentially functionalized porous beads for 45 seconds and prepared the recovered sample for sequencing by adding 8 pmol Lambda16seq (GCCAAAGGCGGTTAAGGTGGTAAT; SEQ ID NO:5) sequencing primer to 10 ng/µl per 100 by of template amplicon. These samples were submitted to the Functional Genomics Center (FGC) at the University of Rochester Medical Center without further processing. In cases where we have benchmarked our results against commercial cleanup kits or other controls, the samples were sent labeled in such a way that we believe could not introduce bias in the sequencing technical staff. The standard protocols are available at the FGC website and entail sequencing on an Applied Biosystems 3700 Prism sequencer using standard Big Dye® labeling chemistry. Our results demonstrate that the efficacy (from the point of view of sequence quality) of cleanup using the differentially functionalized porous beads is similar to that using commercial spin column protocols as determined from a chromatogram generated from the approximate middle of a 1956 by sequence. The chromatogram showed an improvement in peak quality between unpurified and purified samples as exhibited by an increased base fidelity and an improved signal-to-noise ratio. Similar results were observed in more than 5 experiments. In order to further characterize the quality of dsDNA obtained using the method of the invention, we have chosen two standard sequencing metrics, Contiguous Read Length (CRL) and Quality Value higher than 20 (QV20). QV20 is the total number of bases in the entire sequencing trace that have basecaller quality values greater than or equal to 20, those deemed to have probability of assignment error of less than 1%. CRL is the longest uninterrupted stretch of bases with QV higher than a specified limit, in this case 20. In the evaluation of the quality of each base, not only is the quality value of that base used, but also those of adjacent bases within a specified window size. Representative results of trials using these metrics are shown in Table 1. In performing the experiments reported in Table 1, we have used a deliberately "dirty" PCR product sample (i.e., a nominally identical sample without cleanup) where sequencing quality is found to be very poor in the absence of cleanup to increase the stringency of our testing. Excellent sequencing results are obtained with our cleanup method.

TABLE 1

Sequence quality metrics for three PCR runs where different cleanup protocols were employed. For trials I and II, the porous bead treatment uses the protocol of FIG. 4 while trial III uses a pipettor format.

|  | APTMS/ PAA Trial I (Pre-prototype) | | APTMS/ PAA Trial II (Pre-prototype) | | APTMS/ PAA Trial III (Prototype) | |
| --- | --- | --- | --- | --- | --- | --- |
|  | CRL | QV20 | CRL | QV20 | CRL | QV20 |
| No cleanup | 921 | 865 | 51 | 194 | 840 | 843 |
| Spin column (competitor I) | 962 | 978 | 995 | 994 | 960 | 971 |
| Porous bead Treated | 919 | 989 | 884 | 933 | 935 | 932 |

EXAMPLE 2

Preparation and Use of Examples of Differentially Functionalized Nanoporous Materials Prepared Using Electrostatic Assembly of the Non-Pore Coating
Synthesis and Preparation of Nanoporous Materials.

Example 1. 3-Aminopropylsilylated-Silica Gel. With gentle mechanical stirring, Davisil silica gel (25 g, 150 Angstrom pore, 60-200 micron particle size) was suspended in anhydrous toluene (200 mL) under a nitrogen atmosphere. To this was added 3-aminopropyltriethoxysilane (12.5 mL, 53.59 mM) and the mixture heated to reflux. After 6 hours, the mixture was cooled to room temperature and filtered. The resulting 3-aminopropylsilylated-silica gel was then washed with anhydrous toluene (2×100 mL), anhydrous dichloromethane (2×100 mL) and air dried. This material was finally dried to constant weight in a 60° C. oven for 12 hours. Yield 27.5 g.

Matl-1,3-Aminopropylsilylated-Silica Gel-Poly(acrylic acid), $M_w$ 100K. Sodium chloride (1.5 g, 25.7 mM), 4-morpholineethanesulfonic acid x-hydrate (2.44 g) and 35% aqueous poly(acrylic acid), $M_w$=100K, (50 mg) were dissolved in water (200 mL), adjusted to pH 7.0 with 1N-potassium hydroxide and finally made up to 250 mL with water. To the above prepared solution (200 mL) under gentle mechanical stirring, was added 3-aminopropylsilylated-silica gel (2 g). The pH of the supernatant was constantly monitored and rose to approximately 9.0 over a 1 hour period. (If needed, the supernatant's pH may be adjusted to 9.0 by the addition of small amounts of either dilute potassium hydroxide or hydrochloric acid.) After stirring for 1 hour, the 3-aminopropylsilylated-silica gel-poly(acrylic acid) was filtered off, washed with ethanol (30 mL), air dried and finally dried in a 60° C. oven for 1 hour. Yield 1.8 g.

Example 2 Matl-2, 3-Aminopropylsilylated-Silica Gel-Poly(acrylic acid), $M_w$ 450K. An aqueous solution (250 mL) containing sodium chloride (1.5 g, 25.7 mM), 4-morpholineethanesulfonic acid x-hydrate (2.44 g) and poly(acrylic acid), $M_w$ 450K (35 mg) was prepared and adjusted to pH 7.0 with 1N-potassium hydroxide. In an identical procedure to that described in Synthesis Example 1, 3-aminopropylsilylated-silica gel-poly(acrylic acid), $M_w$ 450K was also prepared. Yield 1.8 g.

Example 3. Matl-3, 3-Aminopropylsilylated-Silica Gel-Poly(acrylamide-co-acrylic acid). An aqueous solution (250 mL) containing sodium chloride (1.5 g, 25.7 mM), 4-morpholineethanesulfonic acid x-hydrate (2.44 g) and poly(acrylamide-co-acrylic acid 20:80) (35 mg) was prepared and adjusted to pH 7.0 with 1N-potassium hydroxide. In an identical procedure to that described in Synthesis Example 1, 3-aminopropylsilylated-silica gel-poly(acrylamide-co-acrylic acid) was also prepared. Yield 1.8 g.
Testing.

Analysis of mixtures of biological and chemical compounds oftentimes requires the separation and isolation of their individual components. For example, the analysis and isolation of the newly formed double-stranded DNA (dsDNA) amplicon in polymerase chain reactions (PCR) from the PCR reagents and unwanted side-products. These reagents and unwanted side-products are typically 2'-deoxynucleoside 5'-triphosphates (dNTPs), primers (strands of nucleic acids that serve as starting points for DNA replication) and derivatives thereof.

The materials of the invention were tested for their ability to remove the four dNTPs associated with the amplification of DNA, i.e. 2'-deoxyadenosine 5'-triphosphate (dATP), 2'-deoxycytidine 5'-triphosphate (dCTP), 2'-deoxyguanosine 5'-triphosphate (dGTP) and 2'-thymidine 5'-triphosphate (dTTP). A 10 mM mixture of all four nucleotides can be purchased from Invitrogen, catalogue number 18427-088. This dNTP mixture was diluted 1:250 to give a solution with a final concentration of ~150 μM, useful for testing the ability of the materials of the invention to remove all four nucleotides from the PCR reaction. There is usually some variability in diluting these solutions due to pipetting errors but typically Nano-drop concentrations are 50-100 ng/4, about 5× below a typical starting concentration for dNTPs in a PCR reaction. It should be noted that the term nano-drop is used in conjunction with the NanoDrop 1000 Spectrophotometer, which is an analytical instrument used for measuring the absorbance of very small volumes of solutions, typically 2.5 μL or less and hence the concentration of components in the solutions. The NanoDrop Spectrometer is available for purchase from Thermo Scientific.

To test the ability of the materials of the invention to remove primers or single stranded DNA (ss-DNA) and their derivatives from the PCR reaction, the standard T7 sequence primer was employed. This is a 20 base-pair (bp) primer with the sequence TAA TAC GAC TCA CTA TAG GG (SEQ ID NO:6). It is available from Integrated DNA Technologies and test solutions of ~20 ng/uL, which is roughly 5× a typical starting PCR concentration, were employed.

The ability of the materials of the invention to leave the ds-DNA amplicon untouched and thus separating it from the other components was tested using Lambda-DNA. Lambda is a bacteriophage with a 48 Kb linear double stranded genome. It is widely used as a stock genomic DNA in molecular biology. Invitrogen, catalogue number 15612-013 (Lambda/HindIII), is the genomic lambda-DNA digested by the restriction enzyme HindIII into pieces ranging from 500-23000 bp. Lambda/HindIII is purchased as a stock solution of 500 ng/µL which is then diluted to ~30 ng/µL for nano-drop tests. At 10-50 ng/µL, this is the typical PCR amplicon concentration.

To test the effectiveness of the inventive materials, a 2.5 mg sample was mixed with 25 µL each of the previously described dNTP, ss-DNA or ds-DNA solutions. The suspension was agitated for 30 seconds, briefly centrifuged and a 2.5 µL aliquot removed and its absorbance recorded on the NanoDrop spectrophotometer. To take into account variations in the readings, several tests were carried out for each of the dNTP, ss-DNA and ds-DNA tests and an average calculated. Knowing the absorbance and concentration of the initial stock solutions of dNTP, ss-DNA and ds-DNA, the amount of dNTP, ss-DNA and ds-DNA remaining in the test solutions containing the materials of the invention, can be determined.

To show the effectiveness of the invention, comparison materials Comp-1 and Comp-2 which fall outside the scope of the invention, were prepared and tested. Comp-1 is silica gel that is identical in all aspects to the silica gel used in the preparation of materials of the invention, except that it has not been amino-functionalized, but like Matl-1 it has been exposed to 100K poly(acrylic acid). Comp-2, similar to the invention, is silica gel that has been amino-functionalized as previously described but unlike the invention it has not been treated with poly(acrylic acid).

From Table 1 it can be seen that although Comp-1 does not remove ds-DNA from the test solution, it is also ineffective in removing dNTP and ss-DNA. On the other hand, Comp-2 removes all of the compounds tested. Neither Comp-1 nor Comp-2 is useful, as neither exhibit any selectivity in removing the dNTP, ss-DNA or ds-DNA from solution. However, materials of the invention Matl-1, Matl-2 and Matl-3 that were prepared according to the description of the invention and are both suitably functionalized and treated with a suitable polymer are very effective in removing dNTP and ss-DNA while leaving the ds-DNA in solution.

TABLE 1

Effectiveness of Materials of the Invention.

| Example | Material | % Remaining in Solution | | |
| --- | --- | --- | --- | --- |
| | | dNTP | ss-DNA | Ds-DNA |
| 1 (invention) | Comp-1 | 104* | 99 | 100 |
| 2 (invention) | Comp-2 | 7 | 7 | 5 |
| 3 (invention) | Matl-1 | 2 | 9 | 106* |
| 4 (invention) | Matl-2 | 5 | 8 | 97 |
| 5 (invention) | Matl-3 | 7 | 9 | 101* |

*Falls within experimental error

1. Throughput of PCR Solution Components

Initial studies to determine the efficacy of the beads in removing the various components of PCR product solution were done using a NanoDrop 1000 absorption spectrometer. The NanoDrop data provide quantitative information on the amount of interaction between the individual PCR solution components and the functionalized beads. We measured the amount of purified PCR amplicons, ss-DNA (TAATACGACTCACTATAGGG; SEQ ID NO:1), annealed self-complementary ss-DNA (ATCGTCCTGCAGGACGAT; SEQ ID NO:2) and each dNTP (dATP, dCTP, dGTP and dTTP) retained in solution after ~30 second exposure to the differentially functionalized beads described above. Double strands were represented by New England Biolabs (NEB) Lambda DNA template (NEB N3011S). We used absorbance at 260 nm region as a measure of relative concentration before and after exposure to the beads. In each case, the aforementioned analytes were dissolved in a 20 mM Tris buffer (pH 8.4) with 50 mM $K^+$ and 2 mM $Mg^{2+}$ constituted to simulate the Invitrogen PCR buffer solution and the analyte concentrations were in the neighborhood of what might be expected from PCR product (primer was 10X typical concentration, dNTP was 0.2X typical and amplicons were typical for PCR). The idea behind evaluating Lambda DNA and purified amplicons before and after exposure to the beads was to test ds-DNA retention in solution. The synthetic ss-DNA sequences were intended to simulate primers while the self-complementary sequences simulate incidental primer dimers. We define the latter as primers that complement either parts of themselves or the other primer such that they might form partial duplexes at 25° C.

Amounts of beads used were the same as for example 1, 2.5 mg per 25 microliters of test solution.

Figure 7A:
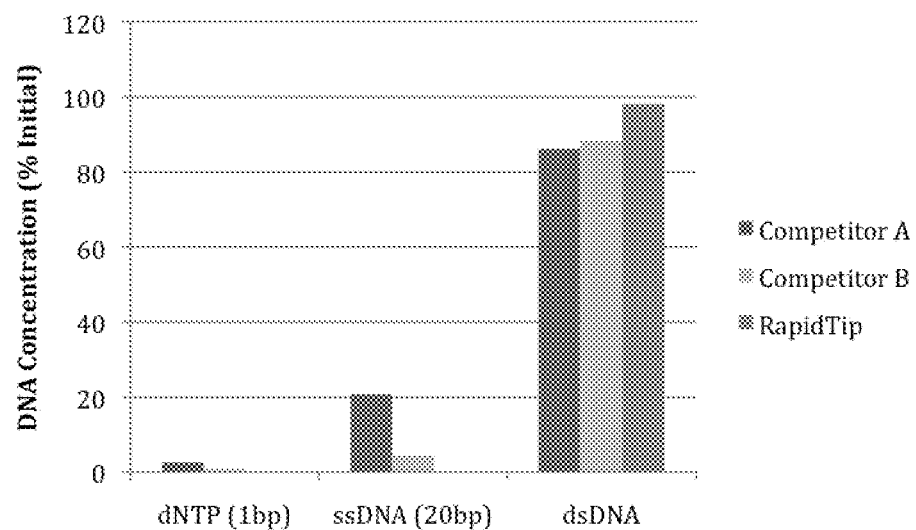
FIG. 7. (a) Graphical representation of data demonstrating that the functionalized nanoporous materials of the present invention can rapidly remove impurities while retaining dsDNA target in solution. Kinetics are measured by mixing single DNA solutions with the functionalized nanoporous materials and aliquoting small volumes of solution at indicated timepoints for analysis on the Nanodrop 1000. The dNTP (nucleotide) and ssDNA (primer) impurites are in dashed lines (black diamond and grey square) while the target is represented with a solid black line and circles. At 60 seconds, typical performance shows >90% retention of target and >90% removal of DNA impurities less than 50 bp. (b) The ds DNA purification has excellent yield. Equal volumes of untreated (−) and treated (with functionalized nanoporous materials) (+) PCR product (0.5 Kb, 1 Kb, and 2 Kb) were run on a 1% agarose gel alongside Invitrogen 1 Kb Plus Ladder (L) and labeled with SybrSafe.

FIG. 7(a) illustrates retention of model primer, dNTP mixture and Lambda ds-DNA demonstrating excellent removal of dNTP and single-stranded DNA and near complete retention of the ds target. Similar solutions were treated with the Invitrogen PureLink PCR Purification (K3100-01) kit ("spin column") and the Promega Wizard analog, the data being shown in the figure.

Figure 7B:
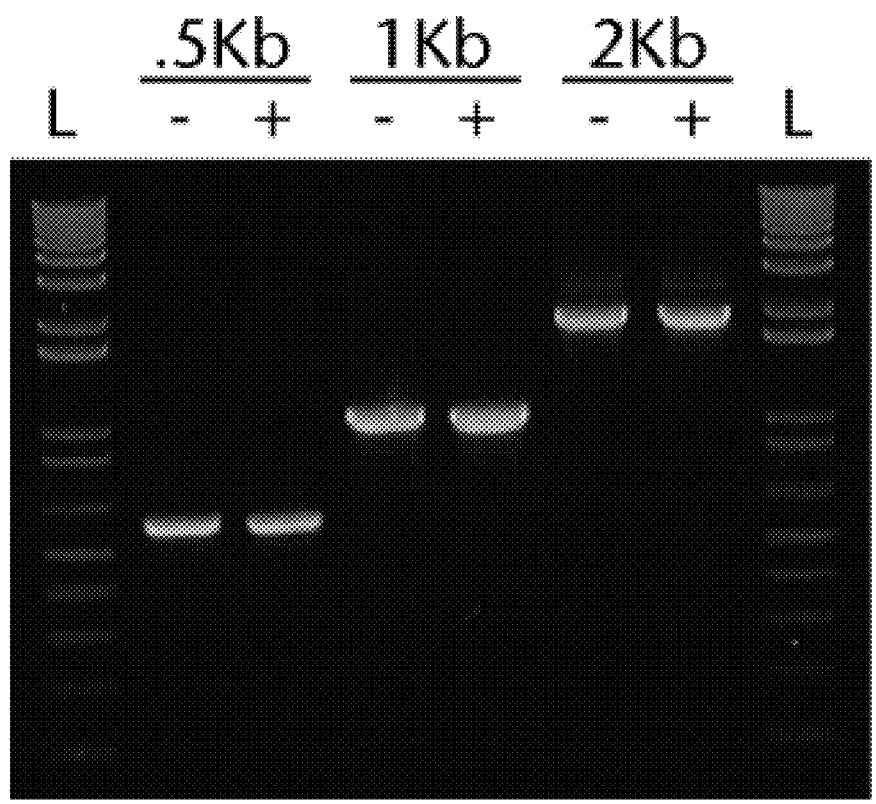

FIG. 7(b) is a comparison between PCR product before and after cleanup using the functionalized nanoporous materials of the present invention demonstrating good DNA throughput regardless of length.

Figure 8:
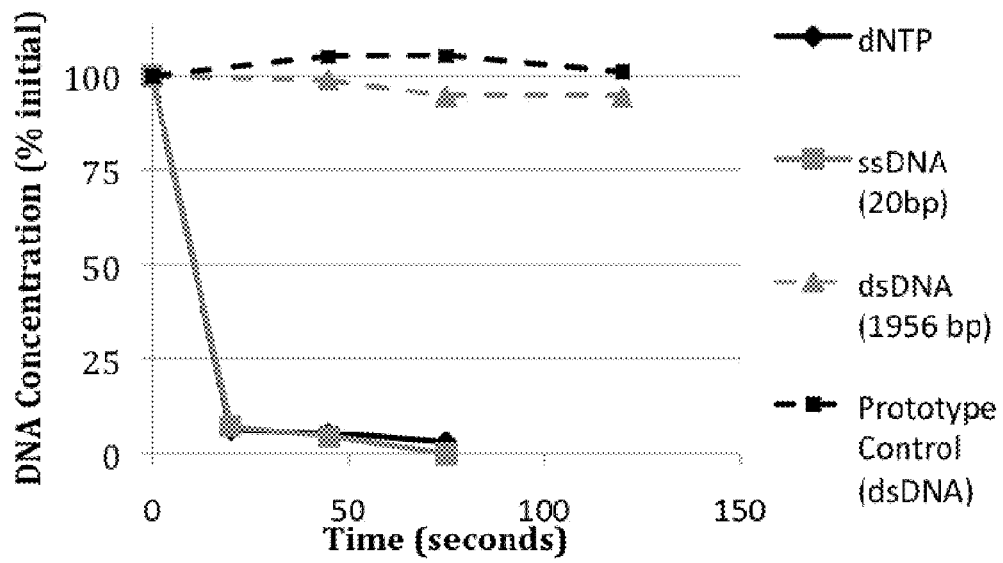
FIG. 8. Graphical representation of adsorption kinetic data for nanoporous materials prepared by electrostatic self-assembly.

Adsorption kinetics data for the particles made by electrostatic self-assembly are shown in FIG. 8. For this measurement, we used the pipette format where we aspirate and eject material since this would be more representative of how we envision customers using the intended product. FIG. 8 presents the kinetics of removing dNTP and ds-DNA from solution using treatments by APTMS/PAA functionalized porous beads. 25 µl dNTP or DNA amplicon solution was aspirated into a pipette tip containing 3.5 mg material (unfunctionalized, diamonds and triangles or functionalized, squares and circles), mixed, and 1 drop was dispensed onto the NanoDrop spectrometer at the indicated times. The data show that optimal times are between 30 and 45 seconds where >95% of the dNTP has been removed and >95% of the amplicons remain. The amplicons remain in solution for at least 10 minutes.

2. Sequencing Following Cleanup

Figure 9:
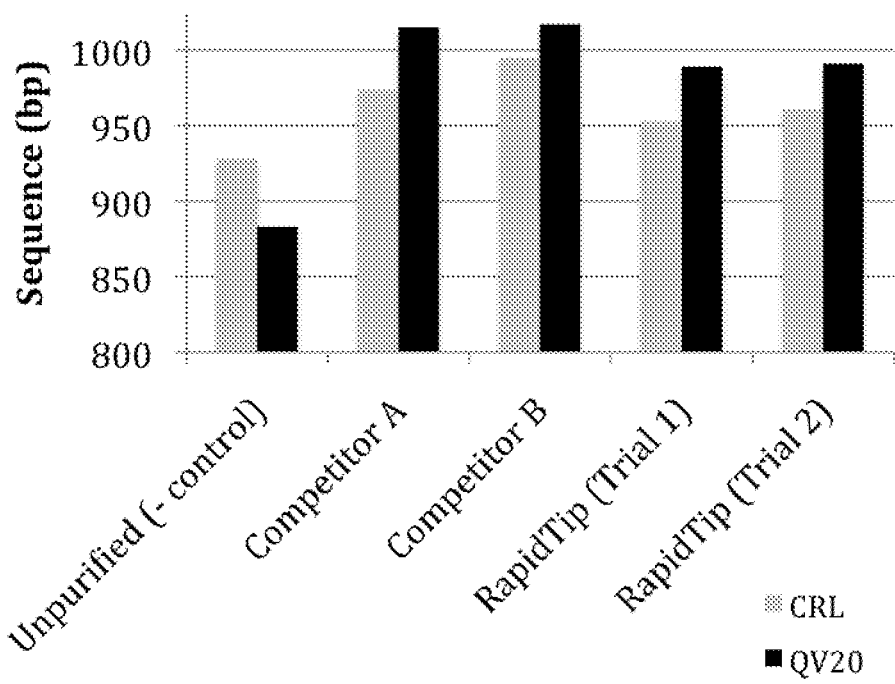
FIG. 9. Sequencing data for PCR solution treated with nanoporous materials of the present invention.

The largest application for cleanup of PCR reactions is use of the amplicons for capillary sequencing. As explained in the section on market need, efficient removal of primers and dNTP is critical. Sequencing results analogous to those shown for the covalently attached materials (see Example 1) are shown in FIG. 9.

EXAMPLE 3

This example demonstrates the removal of the enzyme TAQ polymerase from PCR solutions using hydrophobically coated beads (nanoporous materials).

The protocol used is as follows. In a typical preparation, 0.5 mL of octadecyltrichlorosilane (OTS, SIO6640.0, Gelest, Morrissville, Pa.) was added to 25 mL of EtOH (200 proof) and allowed to stir for 5 minutes in a 50 mL round bottom flask. Silica gel 60 (0.5 g of Merck 9385 or SiliaFlash 60, for example) was added to the flask, and the mixture was refluxed for 0.5 hours. The gel was washed four times with boiling EtOH and dried in an oven for ten minutes at 110° C.

Stock TAQ solution (25 microL) (1:10 dilution) was treated with nanoporous material (2.5 mg) functionalized with OTS in replicates of 2 each. Known TAQ dilutions were measured using absorbance at 280 nm to create a standard curve, which was used to calculate unknown dilutions after treatment.

As the enzymes are much more hydrophobic than ds-DNA and they are adsorbed as is demonstrated in the data depicted in FIG. 11 which are recorded with beads functionalized with octadecyl trichlorosilane.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method for separating double-stranded nucleic acids from a PCR product mixture comprising the double-stranded nucleic acids, single-stranded nucleic acids, and free nucleotides in an aqueous solution comprising the steps of:
   a) contacting the mixture with a spatially inhomogenously functionalized nanoporous material,
      wherein a surface of the spatially inhomogenously functionalized nanoporous material comprises pore surface and non-pore surface and wherein the pore surface has surface groups of a first functionality and the non-pore surface has surface groups of a second functionality that is different than the first functionality,
      wherein the surface groups of the second functionality are provided by individual polymer chains,
      wherein the spatially inhomogenously functionalized nanoporous material is a porous silica,
      wherein the surface groups of the first functionality are amino propyl groups that are covalently bound to the pore surface of the porous silica,
      wherein the surface groups of the second functionality are carboxylate groups or sulfonate groups, and
      wherein the first functionality and the second functionality are the same for all of the spatially inhomogenously functionalized nanoporous material present,
   b) incubating the mixture and the spatially inhomogenously functionalized nanoporous material from a) under conditions such that at least a portion of the single-stranded nucleic acids and free nucleotides are selectively adsorbed to the pore surface; and
   c) isolating the spatially inhomogenously functionalized nanoporous material from the aqueous solution thereby separating at least a portion of the double-stranded nucleic acids in the aqueous solution from the single-stranded nucleic acids and free nucleotides,
   wherein the aqueous solution is incubated with the spatially inhomogenously functionalized nanoporous material for 5 to 60 seconds and greater than 90% of the free nucleotides and single-stranded nucleic acids are removed from and greater than 80% of double-stranded nucleic acids remain in the aqueous solution.

2. The method of claim 1, wherein the pore surface is functionalized with aminopropyltrimethoxysilane and the non-pore surface is functionalized with-compounds selected from the group consisting of poly(acrylic acid, sodium salt) and polystyrene sulfonate.

3. The method of claim 1, wherein the spatially inhomogenously functionalized nanoporous material is isolated from the aqueous solution by centrifugation, filtration, or magnetically.

4. A method for separating double-stranded nucleic acids from a PCR product mixture comprising the double-stranded nucleic acids, single-stranded nucleic acids, and free nucleotides in an aqueous solution comprising the steps of:
   a) contacting the mixture with a spatially inhomogenously functionalized nanoporous material,
      wherein a surface of the spatially inhomogenously functionalized nanoporous material comprises pore surface and non-pore surface and wherein the pore surface has primary amine surface groups and the non-pore surface has surface groups of a functionality that is different than primary amine surface groups,
      wherein the non-pore surface groups are provided by individual polymer chains or preformed polymer chains,
      wherein the primary amine surface groups are covalently bound to the pore surface,
      wherein the spatially inhomogenously functionalized nanoporous material is porous silica,
      wherein the non-pore surface has carboxylate non-pore surface groups or sulfonate non-pore surface groups, and
      wherein the pore surface groups and non-pore surface groups are the same for all of the spatially inhomogenously functionalized nanoporous material present,
   b) incubating the aqueous solution and the spatially inhomogenously functionalized nanoporous material from a) under conditions such that at least a portion of both of the following: single-stranded nucleic acids and free nucleotides are selectively adsorbed to the pore surface; and
   c) isolating the spatially inhomogenously functionalized nanoporous material from the aqueous solution thereby separating at least a portion of the double-stranded nucleic acids from the single-stranded nucleic acids and free nucleotides, wherein the aqueous solution is incubated with the spatially inhomogenously functionalized nanoporous material for 5 to 60 seconds and greater than 90% of the free nucleotides and single-stranded nucleic acids are removed from and greater than 80% of double-stranded nucleic acids remain in the aqueous solution.

5. The method of claim 4, greater than 95% or greater than 99% of the free nucleotides, single-stranded nucleic acids, or both are removed from and greater than 90% of double-stranded nucleic acids remain in the aqueous solution.

6. The method of claim 4, wherein the non-pore surface is functionalized with negatively-charged compounds selected from the group consisting of poly(acrylic acid, sodium salt) and polystyrene sulfonate.

7. The method of claim 4, wherein the spatially inhomogenously functionalized nanoporous material is isolated from the aqueous solution by centrifugation, filtration, or magnetically.

8. A composition comprising a spatially inhomogenously functionalized nanoporous material,
- wherein a surface of the spatially inhomogenously functionalized nanoporous material comprises pore surface and non-pore surface,
- wherein the spatially inhomogenously functionalized nanoporous material has pores of 2 to 300 nm in diameter,
- wherein the pore surface has surface groups of a first functionality and the non-pore surface has surface groups of a second functionality that is different than the first functionality,
- wherein the surface groups of the second functionality are provided by individual polymer chains,
- wherein the spatially inhomogenously functionalized nanoporous material is a porous silica, wherein the surface groups of the first functionality are amino propyl groups that are covalently bound to the pore surface of the porous silica,
- wherein the surface groups of the second functionality are carboxylate groups or sulfonate groups,
- wherein the first functionality and the second functionality are the same for all of the spatially inhomogenously functionalized nanoporous material present, and
- wherein the composition is capable of performing the method of claim 1.

9. The composition of claim 8, wherein the pore surface is functionalized with aminoeropyltrimethoxysilane.

10. The composition of claim 8, wherein the non-pore surface is functionalized with negatively-charged compounds selected from the group consisting of poly(acrylic acid, sodium salt) and polystyrene sulfonate.

11. A composition comprising a spatially inhomogenously functionalized nanoporous material,
- wherein a surface of the inhomogenously functionalized nanoporous material comprises pore surface and non-pore surface,
- wherein the inhomogenously functionalized nanoporous material has pores of 2 to 300 nm in diameter,
- wherein the pore surface has surface groups of a first functionality and the non-pore surface has surface groups of a second functionality that is different than the first functionality,
- wherein the surface groups of the second functionality are provided by individual polymer chains,
- wherein the spatially inhomogenously functionalized nanoporous material is porous silica,
- wherein the surface groups of the first functionality are primary amine groups covalently bound to the pore surface of the porous silica,
- wherein the surface groups of the second functionality are carboxylate groups or sulfonate groups,
- wherein the first functionality and the second functionality are the same for all of the spatially inhomogenously functionalized nanoporous material present, and
- wherein the composition is capable of performing the method of claim 1.

12. The composition of claim 11, wherein the non-pore surface is functionalized with negatively-charged compounds selected from the group consisting of poly(acrylic acid, sodium salt) and polystyrene sulfonate.

* * * * *